US011124815B2

(12) United States Patent
Ernst et al.

(10) Patent No.: US 11,124,815 B2
(45) **Date of Patent: *Sep. 21, 2021**

(54) IMMUNOTHERAPEUTIC POTENTIAL OF MODIFIED LIPOOLIGOSACCHARIDES/LIPID A

(71) Applicants: University of Maryland, Baltimore, Baltimore, MD (US); University of Washington through its Center for Commercialization, Seattle, WA (US)

(72) Inventors: Robert K. Ernst, Silver Spring, MD (US); Mark Pelletier, Brunswick, MD (US); Adeline Hajjar, Seattle, WA (US)

(73) Assignees: UNIVERSITY OF MARYLAND, BALTIMORE, Baltimore, MD (US); UNIVERSITY OF WASHINGTON, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/431,536

(22) Filed: Jun. 4, 2019

(65) Prior Publication Data

US 2019/0367959 A1 Dec. 5, 2019

Related U.S. Application Data

(62) Division of application No. 14/772,282, filed as application No. PCT/US2014/022121 on Mar. 7, 2014, now Pat. No. 10,358,667.

(60) Provisional application No. 61/773,928, filed on Mar. 7, 2013.

(51) Int. Cl.

| | |
|---|---|
| ***C12P 21/00*** | (2006.01) |
| ***C12P 19/26*** | (2006.01) |
| ***A61K 31/715*** | (2006.01) |
| ***C12P 19/12*** | (2006.01) |
| ***A61K 39/02*** | (2006.01) |
| ***A61K 39/39*** | (2006.01) |
| ***A61K 31/739*** | (2006.01) |
| ***C12P 19/44*** | (2006.01) |
| ***C07H 11/04*** | (2006.01) |
| *A61K 39/00* | (2006.01) |

(52) U.S. Cl.

CPC ............ *C12P 19/12* (2013.01); *A61K 31/739* (2013.01); *A61K 39/0291* (2013.01); *A61K 39/099* (2013.01); *A61K 39/39* (2013.01); *C07H 11/04* (2013.01); *C12P 19/26* (2013.01); *C12P 19/44* (2013.01); *A61K 2039/55572* (2013.01)

(58) Field of Classification Search

CPC ..... A61K 31/715; A61K 31/739; C12P 19/12; C12P 19/44; C07H 11/04

USPC .............. 424/279.1; 435/252.3, 100, 254.11, 435/252.34

See application file for complete search history.

(56) References Cited

U.S. PATENT DOCUMENTS

| | | | |
|---|---|---|---|
| 6,548,287 | B1 | 4/2003 | Powell et al. |
| 8,809,285 | B2 | 8/2014 | Guo et al. |

FOREIGN PATENT DOCUMENTS

| | | | |
|---|---|---|---|
| WO | 2007084633 | A2 | 7/2007 |
| WO | 2012141984 | A1 | 10/2012 |

OTHER PUBLICATIONS

Persing et al Trend in Microbiol,2002, 10, pp. 32-37.*
Kanistanon, D. et al., "A Francisella Mutant in Lipid A Carbohydrate Modification Elicits Protective Immunity", PLoS Pathogens, Feb. 8, 2008, vol. 4, pp. 0001-0009.
Persing et al. "Taking Toll: Lipid A Mimetics as Adjuvants and Immunomodulators" Trends in Microbiology. Elsevier Science Ltd, vol. 10, No. 10, Suppl, Jan. 1, 2002, pp. S32-S37, Kidlington. GB.
Raetz et al. "Lipid A Modification Systems in Gram-Negative Bacteria" Annual Review of Biochemistry, vol. 76, No. 1, Jun. 7, 2007, pp. 295-329.
Wang et al. "Lipopolysaccharide: Biosynthetic pathway and structure modification" Progress in Lipid Research, vol. 49, No. 2, Apr. 1, 2010, pp. 97-107.
Wang et al. "MsbA Transporter-dependent Lipid A 1-Dephosphorylation on the Periplasmic Surface of the Inner Membrane: Topography of Francisella Novicida LpxE Expressed in *Escherichia coli*", Journal of Biological Chemistry, vol. 279, No. 47, Nov. 19, 2004, pp. 49470-49478.
Wang, Y. et al., "Attenuated Virulence of a Francisella Mutant Lacking the Lipid A 4'-Phosphatase", PNAS, Mar. 6, 2007, vol. 104, pp. 4136-4141.

* cited by examiner

*Primary Examiner* — Robert B Mondesi
*Assistant Examiner* — Mohammad Y Meah
(74) *Attorney, Agent, or Firm* — Norton Rose Fulbright US LLP

(57) ABSTRACT

Embodiments of the disclosure provide for unique lipooligosaccharide/lipid A-based mimetics for use as adjuvants. Methods of generating lipooligosaccharide/lipid A-based mimetics are provided that utilize recombinantly engineered bacteria to produce the mimetics, including, for example, addition of one or more particular enzymes such as acyltransferases, deacylases, phosphatases, or glycosyltransferases.

5 Claims, 22 Drawing Sheets

WT KIM6
Δ*phoP* tetra-acylated

Δ*phoP*-*pagP*+
*pagP*+ hexa-acylated

MPL

Yp-based LOS/Lipid A Molecules
Biosynthetic Enzymes Modified Indicated

AGP

MPL
(GSK)
[3-7 fatty acids]

Fig. 4. Pathways of adjuvant outcomes for TLR4 activation

| Enzyme/Regulators | Expression | Modification(s) | Location | Outcome | Enzyme[1] |
|---|---|---|---|---|---|
| **Global Regulators** | | | | | |
| PhoP/PhoQ | Addition | C16 fatty acid, aminoarabinose | Acyl-oxy-acyl addition, glucosamine backbone | Increased fatty acid number, carbohydrate residue | YP |
| PmrA/PmrB | Addition | Aminoarabinose | Phosphate residue on glucosamine backbone | Increased carbohydrate residue(s) | YP |
| **Acyltransferases** | | | | | |
| HtrB/LpxL | Addition | C12 fatty acid | Acyl-oxy-acyl addition | Increased fatty acid number | PA |
| MsbB/LpxM | Addition | C14 fatty acid | Acyl-oxy-acyl addition | Increased fatty acid number | PA |
| PagP | Addition | C16 fatty acid | Acyl-oxy-acyl addition | Increased fatty acid number | YP |
| LpxP | Addition | C16:1 fatty acid | Acyl-oxy-acyl addition | Increased fatty acid number | YP |
| LpxA | Addition | O-linked fatty acid | Glucosamine backbone | Altered fatty acid chain length – variable | PA (C10), YP (C14) |
| LpxD | Addition | N-linked fatty acid | Glucosamine backbone | Altered fatty acid chain length – variable | PA (C12), YP (C14) |
| **Phosphatases** | | | | | |
| LpxE | Removal | 1 position phosphate | Glucosamine backbone | Decreased phosphate number – Similar to MPL | FN |
| LpxF | Removal | 4' position phosphate | Glucosamine backbone | Decreased phosphate number | FN |
| **Deacylases** | | | | | |
| PagL | Removal | 3 position fatty acid | Glucosamine backbone | Decreased fatty acid number | ST |
| LpxR | Removal | 3' position fatty acid | Glucosamine backbone | Decreased fatty acid number | ST |
| **Glycosyltransferases** | | | | | |
| PmrK | Addition | Aminoarabinose | Phosphate residue on glucosamine backbone | Increased carbohydrate residue(s) | YP |

[1] Lipid A modification enzyme from this bacterial background: *Pseudomonas aeruginosa* – PA; *Yersinia pestis* – YP; *Francisella novicida* – FN; *Salmonella typhumurium* – ST

FIG. 8

| Temp | Base Strain | Enzymes ( + or Δ) | Enzyme(s) Function | Stucture/Acylation | *m/z* |
|---|---|---|---|---|---|
| 37°C | *Y. pestis* KIM6- | *ΔpagP* | adds C16 | A (tetra) | 1403.8 |
| 37°C | *Y. pestis* KIM6- | *ΔpagP+* | adds C16 | B (hexa, 2 C16) | 1880.3 |
| 37°C | *Y. pestis* KIM6- | *ΔphoP* | global regulator | A (tetra) | 1403.8 |
| 37°C | *Y. pestis* KIM6- | *ΔphoP pagP+* | global regulator/adds C16 | B (hexa, 2 C16) | 1880.3 |
| 37°C | *Y. pestis* KIM6- | *ΔmsbB* | adds C12 | A (tetra) | 1403.8 |
| 37°C | *Y. pestis* KIM6- | *ΔmsbB pagP+* | adds C12/C16 | B (hexa, 2 C16) | 1880.3 |
| 37°C | *Y. pestis* KIM6- | *ΔlpxP* | adds C16:1 | A (tetra) | 1403.8 |
| 37°C | *Y. pestis* KIM6- | *ΔlpxP pagP+* | adds C16:1/ C16 | B (hexa, 2 C16) | 1880.3 |
| 37°C | *Y. pestis* KIM6- | *ΔmsbB ΔlpxP* | adds C12/ C16:1 | A (tetra) | 1403.8 |
| 37°C | *Y. pestis* KIM6- | *ΔmsbB ΔlpxP pagP+* | adds C12/C16:1 C16 | B (hexa, 2 C16) | 1880.3 |
| 37°C | *Y. pestis* KIM6- | *lpxE+* | removes 1 position Phosphate | H ( tetra, -1P) | 1323.8 |
| 37°C | *Y. pestis* KIM6- | *lpxE+ pagP+* | removes 1 position Phosphate/adds C16 | I ( hexa, C12/C16, -1P) | 1800.3 |
| 37°C | *Y. pestis* KIM6- | *lpxF+* | removes 4' position Phosphate | L ( tetra, -1P) | 1323.8 |
| 37°C | *Y. pestis* KIM6- | *lpxF+ pagP+* | removes 4 'position Phosphate/adds C16 | M ( hexa, C12/C16, -1P) | 1800.3 |

ERNST ADJUVANT STRUCTURES

\+ = FUNCTIONAL ENZYME
Δ = LOSS OF ENZYME FUNCTION
STRUCTURE = MAJOR STRUCTURE
ACYLATION = NUMBER OF LIPID A FATTY ACID CHAINS
M/Z = MASS TO CHARGE RATIO

FIG. 9

| Temp | Base Strain | Enzymes ( + or Δ) | Enzyme(s) Function | Stucture/Acylation | *m/z* |
|---|---|---|---|---|---|
| 26°C | *Y. pestis* KIM6- | *ΔpagP* | adds C16 | C (hexa, C12,C16:1) | 1822.2 |
| 26°C | *Y. pestis* KIM6- | *ΔpagP+* | adds C16 | D (hexa, C12,C16) | 1824.3 |
| | | | | | |
| 26°C | *Y. pestis* KIM6- | *ΔphoP* | global regulator | C (hexa, C12,C16:1) | 1822.2 |
| 26°C | *Y. pestis* KIM6- | *ΔphoP pagP+* | global regulator/adds C16 | D (hexa, C12,C16) | 1824.3 |
| | | | | | |
| 26°C | *Y. pestis* KIM6- | *ΔmsbB* | adds C12 | E (penta, C16:1) | 1640.3 |
| 26°C | *Y. pestis* KIM6- | *ΔmsbB pagP+* | adds C12/C16 | F (hexa, C16:1,C16) | 1878.5 |
| | | | | | |
| 26°C | *Y. pestis* KIM6- | *ΔlpxP* | adds C16:1 | G (penta, C12) | 1586 |
| 26°C | *Y. pestis* KIM6- | *ΔlpxP pagP+* | adds C16:1/ C16 | D (hexa, C12, C16) | 1824.3 |
| | | | | | |
| 26°C | *Y. pestis* KIM6- | *ΔmsbB ΔlpxP* | adds C12/ C16:1 | A (tetra) | 1403.8 |
| 26°C | *Y. pestis* KIM6- | *ΔmsbB ΔlpxP pagP+* | adds C12/C16:1 C16 | B (hexa 2 C16) | 1880.3 |
| | | | | | |
| 26°C | *Y. pestis* KIM6- | *lpxE+* | removes 1 position Phosphate | J ( hexa C12,C16:1, -1P) | 1742.3 |
| 26°C | *Y. pestis* KIM6- | *lpxE+ pagP+* | removes 1 position Phosphate/adds C16 | K ( hexa, C12/C16, -1P) | 1744.3 |
| | | | | | |
| 26°C | *Y. pestis* KIM6- | *lpxF+* | removes 4' position Phosphate | N ( hexa C12,C16:1 -1P) | 1742.3 |
| 26°C | *Y. pestis* KIM6- | *lpxF+ pagP+* | removes 4' position Phosphate/adds C16 | O ( hexa, C12/C16, -1P) | 1744.3 |

ERNST ADJUVANT STRUCTURES

+ = FUNCTIONAL ENZYME
Δ = LOSS OF ENZYME FUNCTION
STRUCTURE = MAJOR STRUCTURE
ACYLATION = NUMBER OF LIPID A FATTY ACID CHAINS
M/Z = MASS TO CHARGE RATIO

FIG. 10

HUMAN THP-1 CELL STIMULATION WITH MODIFIED *Y. pestis* KIM6- LOS

| | | | | MyD88 | TRIF/TRAM | TH17 |
|---|---|---|---|---|---|---|
| **Temp** | **Base Strain** | **Enzymes ( + or Δ)** | Stucture / mass | IL-8 | human RANTES | human IL-23p19 |
| 37°C | *Y. pestis* KIM6- | *ΔpagP* | A/ 1403.8 | + | + | + |
| 37°C | *Y. pestis* KIM6- | *ΔpagP+* | B/ 1880.3 | ++++ | +++++ | ++++ |
| 37°C | *Y. pestis* KIM6- | *ΔphoP* | A/ 1403.8 | + | + | N/A |
| 37°C | *Y. pestis* KIM6- | *ΔphoP pagP+* | B/ 1880.3 | ++ | +++ | N/A |
| 37°C | *Y. pestis* KIM6- | *ΔmsbB* | A/ 1403.8 | + | + | N/A |
| 37°C | *Y. pestis* KIM6- | *ΔmsbB pagP+* | B/ 1880.3 | +++ | ++++ | N/A |
| 37°C | *Y. pestis* KIM6- | *ΔlpxP* | A/ 1403.8 | + | + | N/A |
| 37°C | *Y. pestis* KIM6- | *ΔlpxP pagP+* | B/ 1880.3 | ++++ | +++ | N/A |
| 37°C | *Y. pestis* KIM6- | *ΔmsbB ΔlpxP* | A/ 1403.8 | + | + | N/A |
| 37°C | *Y. pestis* KIM6- | *ΔmsbB ΔlpxP pagP+* | B/ 1880.3 | ++++ | ++++ | N/A |
| 37°C | *Y. pestis* KIM6- | lpxE+ | H/ 1328.3 | + | +++++ | ++++ |
| 37°C | *Y. pestis* KIM6- | *lpxE+ pagP+* | I/ 1800.3 | +++++ | +++ | +++ |
| 37°C | *Y. pestis* KIM6- | lpxF+ | L/ 1328.3 | + | +++++ | N/A |
| 37°C | *Y. pestis* KIM6- | *lpxF+ pagP+* | M/ 1800.3 | +++++ | +++ | N/A |
| **CONTROL** | **MPL** | **N/A** | **P/ Variable MZ** | + | + | + |
| **CONTROL** | **Re595** | **N/A** | **Q/ 1797** | +++++ | +++++ | +++ |

ERNST ADJUVANT STRUCTURES

+ = FUNCTIONAL ENZYME

Δ = LOSS OF ENZYME FUNCTION

STRUCTURE = MAJOR STRUCTURE

THP1 (Human acute monocytic leukemia cell line)

FIG. 11

| HUMAN THP-1 CELL STIMULATION WITH MODIFIED *Y. pestis* KIM6- LOS | | | | | |
|---|---|---|---|---|---|
| | | | | MyD88 | TRIF/TRAM |
| Temp | Base Strain | Enzymes ( + or Δ) | Stucture / mass | IL-8 | human RANTES |
| 26°C | *Y. pestis* KIM6- | Δ*pagP* | C/ 1822.2 | ✦✦✦✦ | ✦✦✦✦ |
| 26°C | *Y. pestis* KIM6- | Δ*pagP*+ | D/ 1824.3 | ✦✦✦✦✦ | ✦✦✦✦✦ |
| 26°C | *Y. pestis* KIM6- | Δ*phoP* | C/ 1822.2 | ✦✦✦ | ✦✦✦ |
| 26°C | *Y. pestis* KIM6- | Δ*phoP pagP*+ | D/ 1824.3 | ✦✦✦ | ✦✦ |
| 26°C | *Y. pestis* KIM6- | Δ*msbB* | E/ 1640.3 | ✦✦ | ✦✦ |
| 26°C | *Y. pestis* KIM6- | Δ*msbB pagP*+ | F/ 1878.5 | ✦✦✦✦ | ✦✦✦✦✦ |
| 26°C | *Y. pestis* KIM6- | Δ*lpxP* | G/ 1586 | ✦ | ✦ |
| 26°C | *Y. pestis* KIM6- | Δ*lpxP pagP*+ | D/ 1824.3 | ✦✦ | ✦ |
| 26°C | *Y. pestis* KIM6- | Δ*msbB* Δ*lpxP* | A/ 1403.8 | ✦ | ✦ |
| 26°C | *Y. pestis* KIM6- | Δ*msbB* Δ*lpxP pagP*+ | B/ 1880.3 | ✦✦✦ | ✦✦ |
| 26°C | *Y. pestis* KIM6- | *lpxE*+ | J/ 1742.3 | ✦✦✦✦ | ✦✦✦✦✦ |
| 26°C | *Y. pestis* KIM6- | *lpxE*+ *pagP*+ | K/ 1744.3 | ✦✦✦ | ✦✦✦ |
| 26°C | *Y. pestis* KIM6- | *lpxF*+ | N/ 1742.3 | ✦✦✦ | ✦✦✦ |
| 26°C | *Y. pestis* KIM6- | *lpxF*+ *pagP*+ | O/ 1744.3 | ✦✦✦✦ | ✦✦✦✦✦ |
| **CONTROL** | **MPL** | **N/A** | **P/ Variable MZ** | ✦ | ✦ |
| **CONTROL** | **Re595** | **N/A** | **Q/ 1797** | ✦✦✦✦✦ | ✦✦✦✦✦ |

ERNST ADJUVANT STRUCTURES

\+ = FUNCTIONAL ENZYME
Δ = LOSS OF ENZYME FUNCTION
STRUCTURE = MAJOR STRUCTURE
M/Z = MASS TO CHARGE RATIO
✦ =IMMUNOSTIMULATORY ABILITY AS DECTED BY ELISA
THP1 (Human acute monocytic leukemia cell line)

FIG. 12

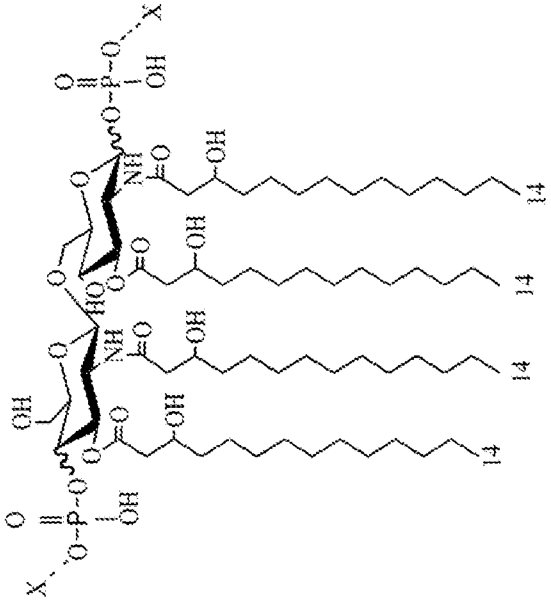
Structure A
**1403.8 *m/z***
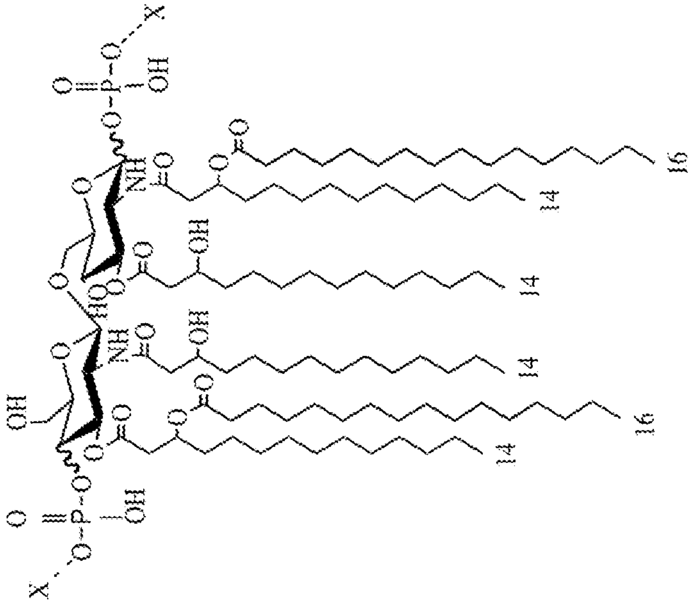
Structure B
**1880.3 *m/z***
FIG. 13

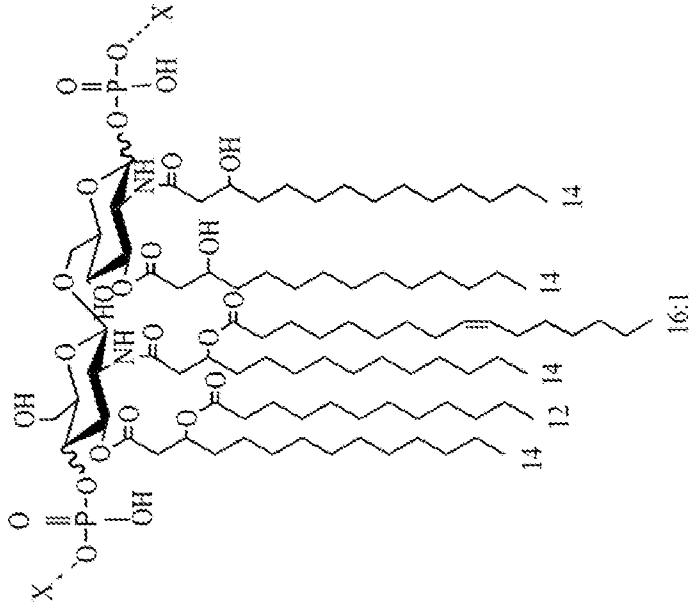
Structure C
**1822.2 *m/z***
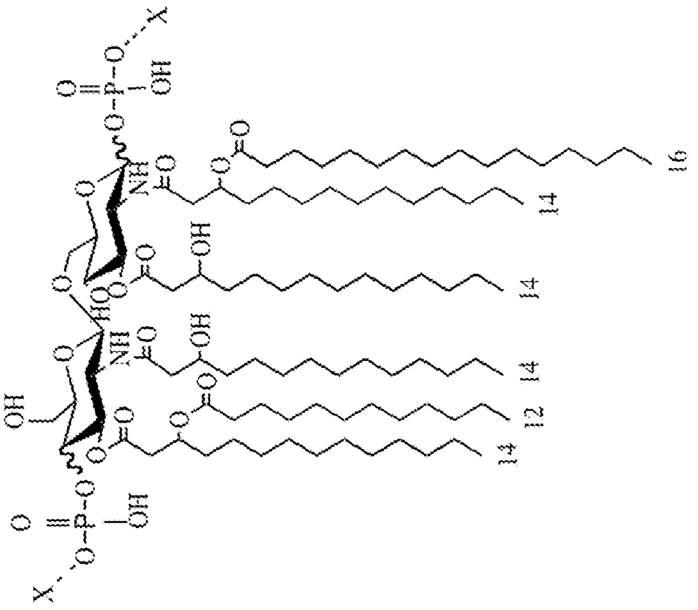
Structure D
**1824.3 *m/z***
FIG. 14

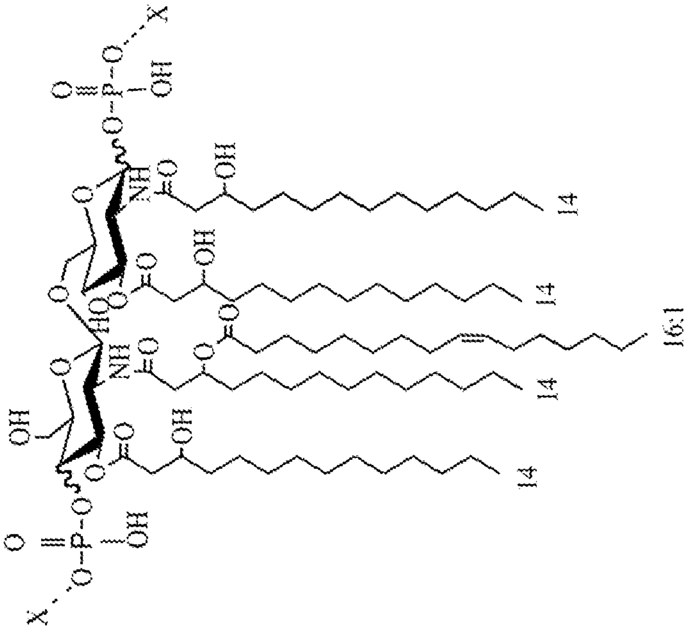
Structure E
**1640.3 *m/z***
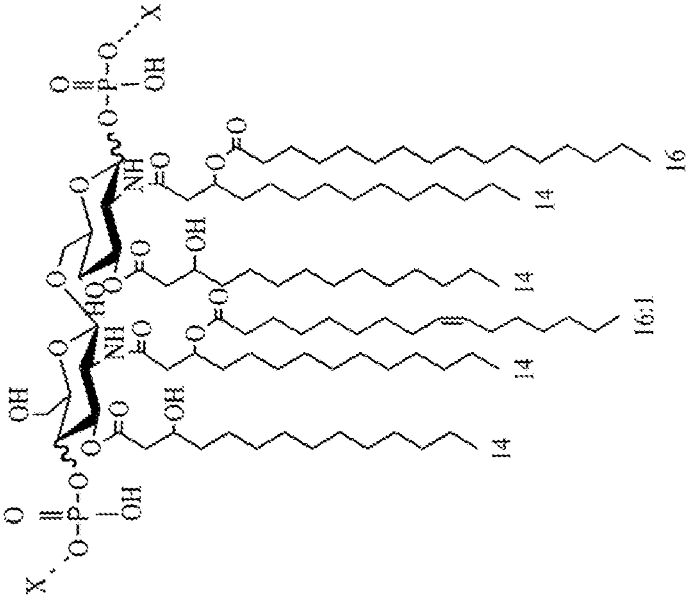
Structure F
**1878.54 *m/z***
FIG. 15

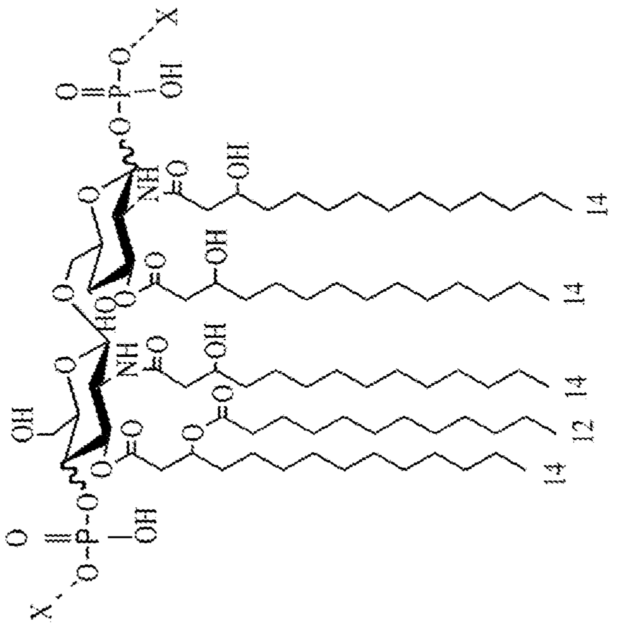
Structure G
**1586 *m/z***
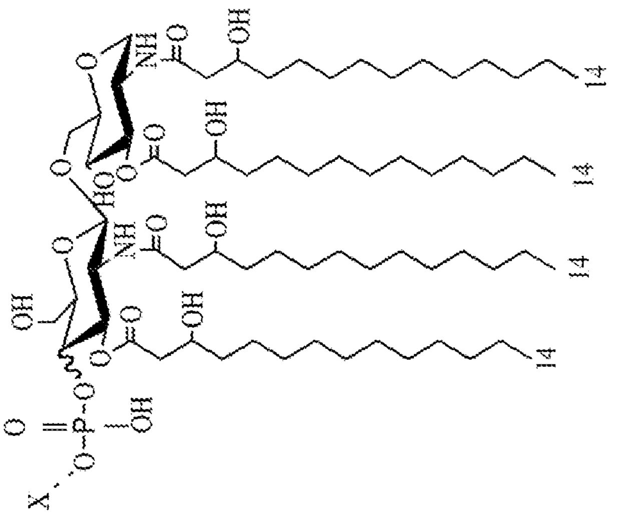
Structure H
**1323.8 *m/z***
FIG. 16

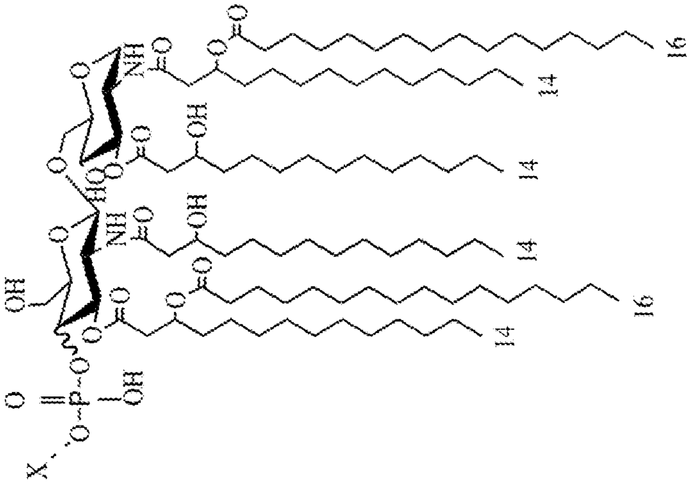
Structure I
**1800.3 *m/z***
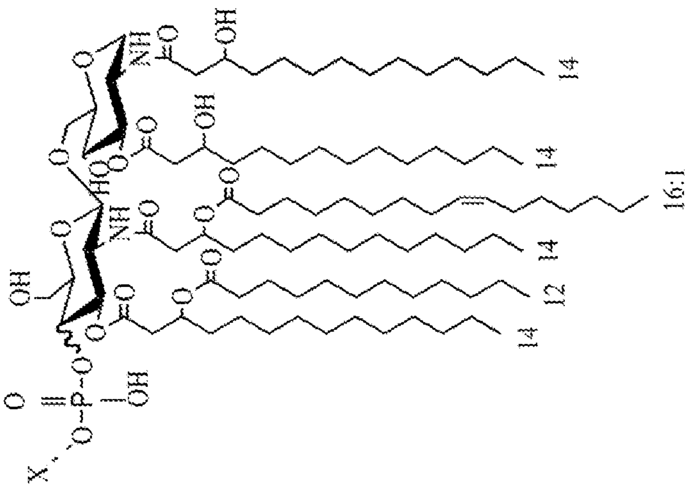
Structure J
**1742.3 *m/z***
FIG. 17

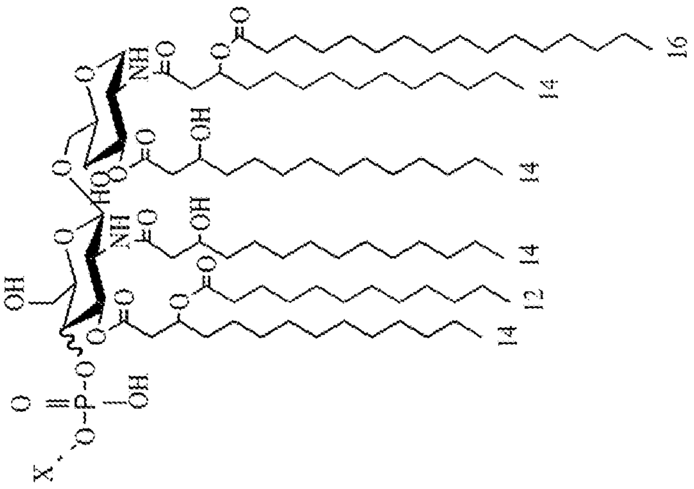
Structure K
**1744.3 *m/z***
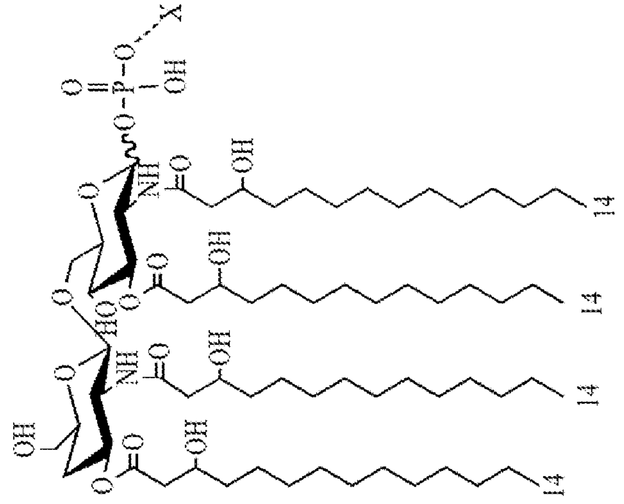
Structure L
**1323.8 *m/z***
FIG. 18

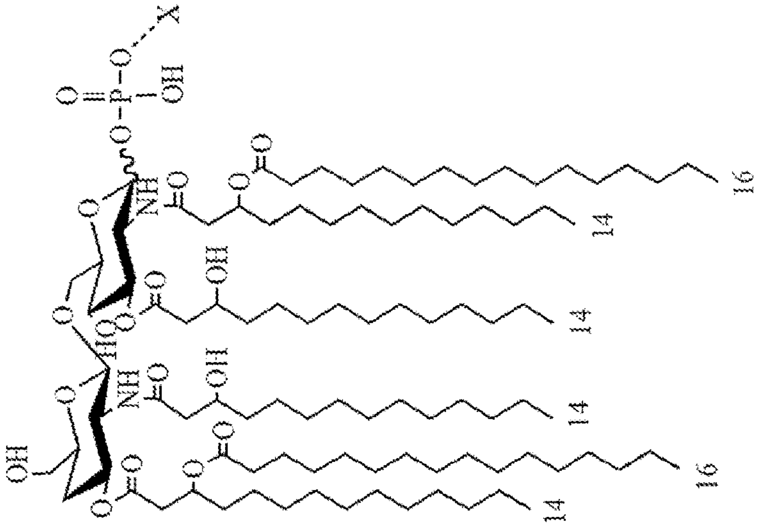
Structure M
**1800.3 *m/z***
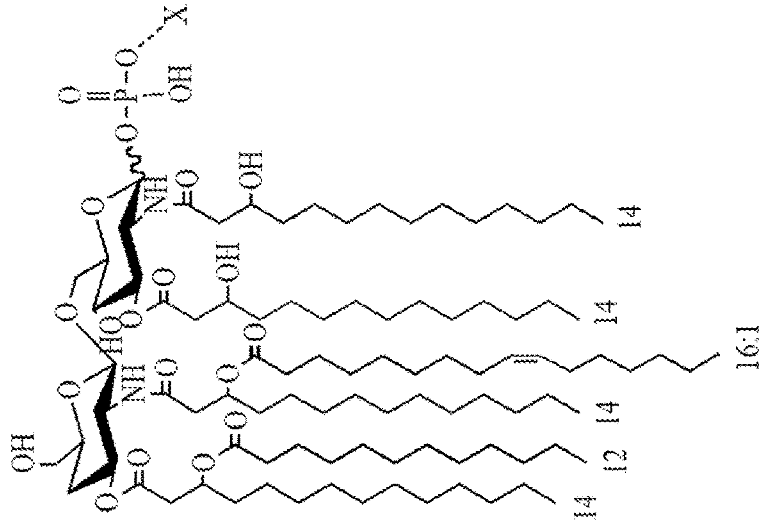
Structure N
**1742.3 *m/z***
FIG. 19

Structure O

**1744.3 *m/z***

Monophosphoryl Lipid A (MPL)
**Mixture Of Various *m/z* species**
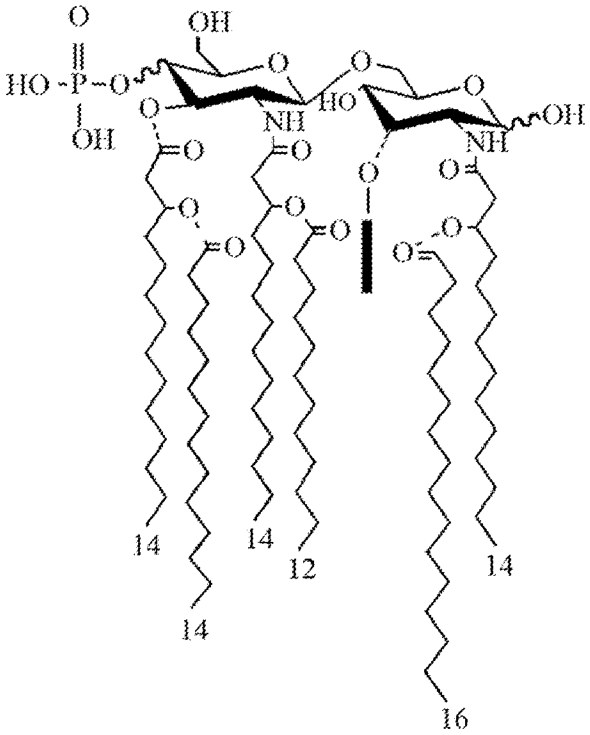
Structure P
▌= Chains with varying lengths
**Re595 *S. minnesota***
***(*Rough LPS) Lipid A**
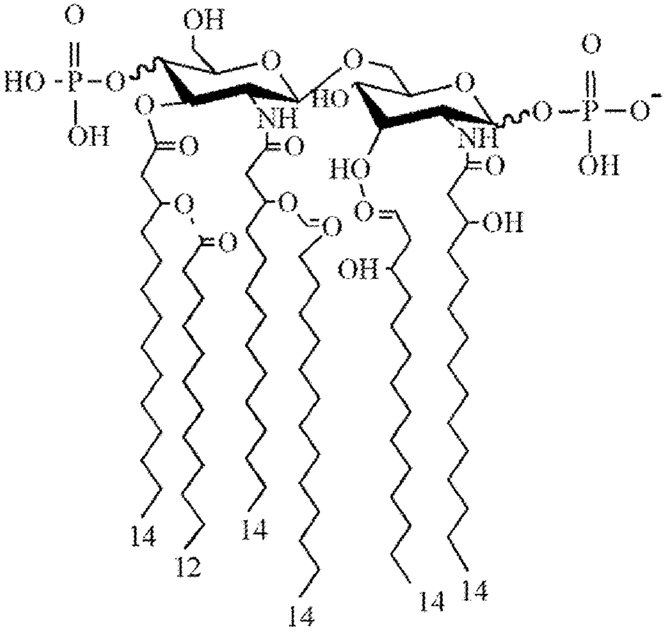
Structure Q
**1797 *m/z***
FIG. 21

IMMUNOTHERAPEUTIC POTENTIAL OF MODIFIED LIPOOLIGOSACCHARIDES/LIPID A

CROSS-REFERENCE TO RELATED APPLICATIONS

This application is a divisional of U.S. Non-Provisional patent application Ser. No. 14/772,282 filed Sep. 2, 2015, now U.S. patent Ser. No. 10/358,667, which is a national phase application under 35 U.S.C. § 371 that claims priority to International Application No. PCT/US2014/022121 filed Mar. 7, 2014 which claims the benefit of priority to U.S. Provisional Patent Application No. 61/773,928, filed Mar. 7, 2013, all of which application is are incorporated by reference herein in its their entirety.

STATEMENT REGARDING FEDERALLY SPONSORED RESEARCH OR DEVELOPMENT

This invention was made with government support under Grant Number AI101685 awarded by The National Institutes of Health. The government has certain rights in the invention.

TECHNICAL FIELD

Embodiments of the disclosure generally relate at least to the fields of immunology, cell biology, molecular biology, and medicine. The present disclosure generally relates to compositions, methods of screening, and methods of use for immunotherapeutic molecules and adjuvants for immunogenic formulations. More specifically, the present invention relates to compositions and methods of screening for immunogenic formulations using bacterial enzymatic combinatorial chemistry.

BACKGROUND OF THE INVENTION

To date, vaccine adjuvants such as complete Freund's adjuvant derived from the cell wall of mycobacteria in a water-in-oil emulsion or aluminum salts have been developed using an empirical trial-and-error approach. This approach has identified compounds that compensate for poor immune responsiveness to an antigen, increase vaccine stability, and reduce the dose of an antigen required for protection, though the exact immunological mechanism for their function in the host is still under debate. However, identifying or developing new, rationally-designed adjuvant(s) that stimulate components of the host innate and/or adaptive immune systems, based on known correlates of immune protection are now possible with efficacy and safety being the primary goals. The significance of identifying novel adjuvants is highly important as most of the current trends in vaccine development are based on poorly immunogenic, highly purified antigens, which will require an appropriate adjuvant to induce an effective protective immunity.

An area of great interest is in the development of more rationally-designed adjuvants based on molecules that stimulate the host innate immune system, specifically pattern-recognition receptors, including toll-like receptors (TLR). The TLR family plays a critical role in early innate immunity by acting as sensors in response to invading pathogens and are expressed in tissues involved in immune function, e.g. peripheral blood leukocytes and spleen or those exposed to the external environment like the gastrointestinal tract and lung. To date, ten human and twelve murine TLRs have been identified with most localized to the cell plasma membrane with the exception of TLR3, TLR7, TLR8, and TLR9 being localized intracellularly. Each receptor recognizes highly conserved structural motifs expressed by microbial pathogens (PAMPs) that are different from host ligands. Briefly, TLR2 is essential for the recognition of bacterial lipoproteins, lipoarabinomannans and lipoteichoic acids from Gram-positive organism; TLR3 recognizes viral dsRNA; TLR5 detects flagellin, the major protein subunit of flagella; TLR9 recognizes hypo-methylated CpG DNA motifs; TLR7 and TLR8 recognize small synthetically derived viral RNAs; TLR4 is activated by LPS through its bioactive component lipid A or endotoxin, in conjunction with the accessory molecules, MD-2 and CD14 that form a complex with TLR4. Finally, TLR signaling specificities are extended by their ability to heterodimerize (they mostly homodimerize, but TLR2 heterodimerizes) with one another. Stimulation of TLRs by PAMPs initiates signaling cascades that involve a number of proteins, such as MyD88, TRIF and IRAK (Kawai and Akira, 2011; Pasare and Medzhitov, 2005). These signaling cascades lead to the activation of transcription factors, such as AP-1, NF-κB and IRFs inducing the secretion of pro-inflammatory cytokines, chemokines, and effector cytokines that direct or modify the host immune response. Among TLRs, only TLR3 and TLR4 stimulate the production of type I IFNs via TRW and the induction of a robust IL-12p70 response that strongly enhances cellular-mediated and humoral immune responses.

Currently, a number of TLR mimetics are being used as stand-alone immunotherapeutic adjuvants or in combination with TLR signaling molecules. Examples include natural and synthetic-based lipid A mimetics, monophosphoryl lipid A (MPL) and aminoalkyl glucosaminide phosphates (AGPs). MPL is a chemically modified form of lipid A, derived from *Salmonella minnesota* R595 lipopolysaccharide. These chemical modifications result in the generation of a 4'-monophosphoryl, 3-O-deacylated lipid A structure that also displays differences in the overall number and location of individual fatty acids attached to the glucosamine sugar backbone of lipid A. As MPL is chemically derived, lot-to-lot differences in the microheterogeneity of the acyl groups make performing structure-activity relationship studies problematic. In contrast, the AGP classes of lipids are monosaccharide lipid A mimetics based on the biologically active hexa-acylated component present in MPL, chemically synthesized with modifications in the acyl chain length and location in uniform positions. Both molecules display low-toxicity, as compared to LPS (approximately 0.1% as toxic as LPS for MPL) and are potent immunostimulators of the host innate and adaptive immune system. Assessment of the adjuvant characteristics of MPL has shown it to be an effective adjuvant for the induction of both humoral and cell-mediated immunity in which MPL can induce both $Th_1$- and $Th_2$-type immune responses in the systemic and mucosal compartments of the immune system. MPL is currently a component in many of GalaxoSmithKline's (GSK) proprietary and novel adjuvant systems used in multiple GSK Bio vaccines. However, due to the increased heterogeneity from the chemical hydrolysis of lipid A for the production of MPL and the limitations and labor intense nature of synthesizing AGPs that more closely mimic the structure of naturally occurring lipid A structures, alternative technologies are in need.

BRIEF SUMMARY OF THE INVENTION

Protection from infectious agents known to be major causes of death worldwide, such as influenza, tuberculosis, and malaria, as well as potential release of bioweaponized agents that cause plague, tularemia, and melioidosis, require vaccines that generate humoral and T-cell responses. Effective component vaccines require the addition of adjuvants to increase their immunogenic capacities. Until recently, alum salts, which require repeated applications and tend to be skewed towards T helper TH 2-based immunity (humoral) rather than TH 1, (cellular) were the only adjuvants approved for use in human vaccines. Recently, the lipid A mimetic (monophosphoryl lipid A, MPL) adjuvant has been combined with alum (AS04) in two FDA-approved vaccines (Cervarix (Human Papilloma Virus), and Fendrix (Hepatitis B Virus)). Additionally, synthetic lipid A mimetics aminoalkyl glucosaminide phosphates (AGPs) that also signal through Toll-Like Receptor 4 (TLR4) are being studied as both adjuvants or stand-alone immunogenic compounds. Thus, TLR4 agonists show great promise for use as adjuvants in component vaccines. However, the approved TLR4 agonist, MPL, has distinct deficiencies both in potency and structural consistency, and AGPs are labor intensive and costly to synthesize.

The present disclosure is directed to compositions and methods related to immunological compositions and synthesis thereof, including compositions and methods related to adjuvants and their methods of making them. Kits including the adjuvants are encompassed in the disclosure. In particular embodiments, there are methods and compositions related to modified lipooligosaccharides/Lipid A molecules as adjuvants; the compositions may be considered to be lipooligosaccharide/lipid A-based immunomodulators or lipooligosaccharide/lipid A-based immunopotentiators.

Provided herein is a novel approach of using Bacterial Enzymatic Combinatorial Chemistry (BECC) to make rationally-designed lipid A structures by modifying the lipid A structure of a lipopolysaccharide (LPS) or lipooligosaccharide (LOS) from a Gram negative bacteria (such as an attenuated (BSL-2 approved) *Yersinia pestis* (Yp) strain). In general aspects, this approach uses the lipid A structure present in LPS/LOS synthesized in bacteria as a lead molecule or structure to be modified by heterologous in trans expression of lipid A biosynthesis enzymes. These enzymes are obtained from a wide variety of bacterial backgrounds with specificities for the removal or addition of fatty acid chain, phosphates moieties, and carbohydrates to the lipid A backbone. In particular aspects, one approach uses the non-stimulatory, hypoacylated, and bisphosphorylated lipid A structure present in LOS synthesized by a Yp strain. As such, methods of the disclosure allow for the safe, cost effective, and efficient design of molecules with immunostimulatory use. One can test the immunotherapeutic use of these new molecules in vitro and in vivo to identify novel molecules representing adjuvants and/or immunomodulating reagents. One can also include well-characterized immunostimulants, such as MPL and known LPS structures, as comparisons to the molecules synthesized by BECC. The protective innate/adaptive immune responses by this novel approach of creating new adjuvants has important implications at least in the fields of antigen recognition, formulation, and vaccine design.

One embodiment of the disclosure comprises a variety of modified lipooligosaccharides comprising core regions of LPS and lipid A molecules, wherein the structures have adjuvant-like properties; in at least some regards, the compositions are lipooligosaccharide/lipid A-based agonists. In specific embodiments, the structures are TLR4-signaling molecules. Certain properties for the lipooligosaccharides/Lipid A molecules that are useful include having a detectable proinflammatory response but low adverse reaction for an individual. Particular embodiments allow establishment of a novel mechanism for adjuvant/vaccine design leading to well-defined, outcome-specific adjuvants that can elicit cellular immunity ($T_H1$ and $T_H17$-type immune responses) in addition to robust antibody production in the systemic and mucosal compartments of the host. In specific embodiments, when the compositions are administered with an antigen, antigen-specific adaptive responses, TH1 and/or TH2 and/or antibodies are produced.

In embodiments of the disclosure, rationally-designed adjuvants based on molecules that stimulate the host innate immune system are used alone or in other immunogenic compositions to combat disease. Provided herein are chemically defined lipooligosaccharide/lipid A-based adjuvants that are safe, easy to produce, and effective in conferring protection against a wide variety of pathogenic bacteria and viruses, for example. With methods of the invention, one can engineer a wide range of adjuvant molecules for use either as stand-alone immunotherapeutic molecules or adjuvants in immunogenic compositions, including vaccine formulations, for example.

Provided herein are oligosaccharides with modified lipid A structures that are immunogenic. Also provided are methods of screening for immunotherapeutic molecules and adjuvants for formulations of immunogenic compositions, including vaccine compositions. Further, the present disclosure provides methods for using the identified compounds for immunotherapy as immunotherapeutic molecules and adjuvants—for vaccine formulations. In one embodiment of the disclosure, methods of synthesizing structures are described using biosynthesis pathways present in Gram-negative bacteria based on the presence or absence of specific phosphate, acyl, and carbohydrate groups, as an example of modifications. Particular aspects of the methods involve the de novo synthesis of lipid A-like compositions in a Gram-negative bacteria, as opposed to modifications of a known or existing molecule.

In one embodiment of the disclosure, there are methods of screening for immunotherapeutic molecules and adjuvants for vaccine formulations.

Embodiments of the disclosure exploit the lipid A biosynthetic pathway of a Gram negative bacteria for the synthesis of novel TLR4-based immunostimulators. In certain aspects, the disclosure provides an understanding of the molecular basis by which Gram-negative bacteria modify the lipid A component of lipopolysaccharide (LPS) and how these alterations affect or circumvent normal host innate immune system responses. These modifications can promote resistance to host innate immune killing mechanisms by antimicrobial compounds and alter recognition by TLR4.

Particular aspects include modifications of LPS, the major component of the Gram-negative bacterial envelope, from *P. aeruginosa, Francisella* subspecies, *Bordetella* subspecies, *S. typhimurium, Acinetobacter baumannii, Burkholderia*, and *Yersiniae* subspecies, and in specific aspects the lipid A component of LPS is altered in one or more of these bacteria using methods of the disclosure.

Embodiments of the disclosure include administering a therapeutically effective amount of at least one modified lipooligosaccharide/lipid A composition to an individual in need thereof. The administration may be by any route, although in particular embodiments a variety of administrative routes (intramuscular, intravenous, intranasal, aerosol, subcutaneous, intraperitoneal, intradermal, for example) are employed.

The structure and/or function of lipooligosaccharide/lipid A-based mimetics of the disclosure may be modified as compared to a host bacteria in which the composition is generated or as compared to a reference molecule, such as MPL. In specific aspects, candidate adjuvant molecules are tested in vivo, including, for example, via an intranasal route and, optionally, a subsequent intramuscular route. In certain cases, there is use of tissue culture cell lines (human and murine TLR4) as well as primary dendritic cells (human and murine-derived) to evaluate toxicity and proinflammatory responses to the BECC-synthesized molecules.

The modifications in the lipooligosaccharide/lipid A-based mimetics may be of any kind, including modifications to the fatty acid content and/or number, the number of phosphates and/or modification thereof, and the number or type of sugar. In certain embodiments, the construction of new BECC-synthesized adjuvant molecules concern altering the terminal phosphates on the glucosamine backbone of lipid A that is useful for eliciting innate immune responses.

In specific aspects, the bacteria is an Archaebacteria. In specific embodiments, the bacteria is an extremophile, including an Acidophile; Alkaliphile; Anaerobe; Cryptoendolith; Halophile; Hyperthermophile; Hypolith; Lithoautotroph; Metallotolerant; Oligotroph; Osmophile; Piezophile; Polyextremophile; Psychrophile/Cryophile; Radioresistant; Thermoacidophile; or Xerophile, for example.

In particular aspects, the bacteria in which the lipooligosaccharide/lipid A-based mimetics are generated is an avirulent *Y. pestis* strain, such as one that has lost one or more virulence plasmids. In specific embodiments, the strain is wild-type *Y. pestis* KIM6, although any number of the modified KIM6 strains may be employed (e.g., KIM6 del PhoP (regulator) could be made with LpxF+(expressing a phosphatase) or KIM6 del LpxD (acyltransferase) could be made with a del PmrK (which would not add aminoarabinose).

In one embodiment, there is a method of generating a lipooligosaccharide/lipid A-based mimetic, comprising the steps of obtaining a bacterial strain that has one or more of the following modifications: expresses one or more non-endogenous lipid A biosynthesis enzymes; expresses one or more endogenous lipid biosynthesis enzymes, wherein the enzyme is modified; and/or has modified regulation of one or more endogenous lipid biosynthesis enzymes; and subjecting the strain to conditions suitable for production of the lipooligosaccharide/lipid A composition. In particular embodiments, the obtaining step is further defined as engineering the bacterial strain to have one or more of the modifications. In some cases, the engineering step comprises one or more of delivering a vector into the bacteria; and/or bacterial conjugation. In specific embodiments, the engineering step comprises delivering a vector into the bacteria, wherein the vector comprises sequence that encodes one or more non-endogenous lipid A biosynthesis enzymes. In specific embodiments, the one or more non-endogenous lipid A biosynthesis enzymes is an acyltransferase, deacylase, phosphatase, glycosyltransferase, or a mixture thereof, from another bacterial strain. In particular embodiments, the engineering step comprises modifying the bacteria to express a modified endogenous lipid biosynthesis enzyme. In some cases, the modified endogenous lipid biosynthesis enzyme comprises a mutation in the enzyme. In certain embodiments, the one or more modified endogenous lipid biosynthesis enzymes is an acyltransferase, deacylase, phosphatase, or glycosyltransferase. In some cases, the engineering step comprises modifying the bacteria to have modified regulation of expression of one or more endogenous lipid A biosynthesis enzymes. In specific embodiments, modifying the bacteria to have modified regulation of expression of one or more endogenous lipid biosynthesis enzymes is further defined as mutating a gene in the bacteria that is a regulatory gene for lipid A biosynthesis in the bacteria, including one defined as a sensor kinase, a response regulator, or both of a two-component regulatory system in the bacteria. In certain cases, the regulatory gene for lipid A biosynthesis is histidine kinase. In some cases, the one or more endogenous lipid biosynthesis enzymes is an acyltransferase, deacylase, phosphatase, or glycosyltransferase. In particular embodiments, the subjecting step comprises particular temperature conditions suitable for production of the lipooligosaccharide/lipid A composition.

In certain embodiments of methods of generating a lipooligosaccharide/lipid A-based mimetic, the lipooligosaccharide/lipid A-based mimetic produced by the method has a modified level and/or content of fatty acid compared to the endogenous bacterial lipid A molecule or a reference lipid A molecule. In particular embodiments, the lipooligosaccharide/lipid A-based mimetic produced by the method has a modified number of phosphates compared to the endogenous bacterial lipid A molecule or a reference lipid A molecule. In certain embodiments, the lipooligosaccharide/lipid A-based mimetic produced by the method has modified phosphates compared to the endogenous bacterial lipid A molecule or a reference lipid A molecule. In particular aspect, the modified phosphates are further defined as having only one sugar (simple and aminosugars) or having an additional sugar linked to the phosphate or ethanolamine. In specific aspects, the lipooligosaccharide/lipid A-based mimetic produced by the method has a modified sugar number and/or content compared to the endogenous bacterial lipid A molecule or a reference lipid A molecule. In some cases, the lipooligosaccharide/lipid A-based mimetic comprises one or three or more sugars. The lipooligosaccharide/lipid A-based mimetic may comprise modified sugars selected from the group consisting of aminoarabinose, glucosamine, and galactosamine. In some cases, the method further comprises the step of analyzing extracts from the bacteria for the structure, function, or both of the lipooligosaccharide/lipid A-based mimetic.

In specific aspects, the analyzing step comprises analyzing the structure of the lipooligosaccharide/lipid A-based mimetic by performing one or more types of mass spectrometry, gas chromatography, or a combination thereof. In some cases, the analyzing step comprises analyzing the function of the lipooligosaccharide/lipid A-based mimetic by measuring an inflammatory response of the lipooligosaccharide/lipid A-based mimetic. In particular embodiments, the inflammatory response is a proinflammatory response, such as one measured by cell stimulation of macrophages. The proinflammatory response may be measured by activation of cell-mediated pathways, humoral pathways, or both.

In some embodiments of methods of generating a lipooligosaccharide/lipid A-based mimetic, the bacterial strain is *Yersinia pestis, Pseudomonas*, an Archaebacteria or an extremophile. In specific embodiments, the one or more non-endogenous lipid A biosynthesis enzymes is from *Pseudomonas aeruginosa, Francisella novicida, E. coli, Bordetella subspecies, Helicobacter pylori*, or *Salmonella typhimurium*. In some aspects of the method, the method further comprises the step of combining the lipooligosaccharide/lipid A-based mimetic with an antibody, a weakened microbe, a killed microbe, one or more antigens, a toxoid, polysaccharide, or nucleic acid to produce an immunogenic composition. In some cases, the method further comprises the step of delivering an effective amount of the immunogenic composition to an individual in need thereof.

In some embodiments, the composition is a compound of formula (I)

(I)

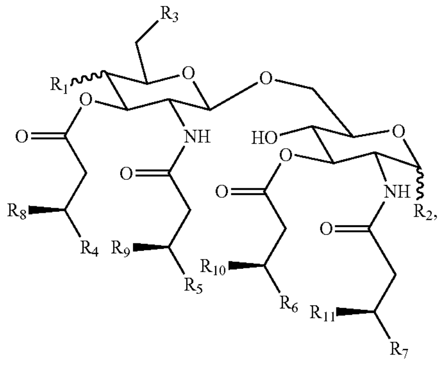

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons (for a chain of 16 carbons), and $R_8$, $R_9$, $R_{10}$ and $R_{11}$ may be H, OH, or an alkyl or alkenyl ester of up to 16 carbons.

In some embodiments, there is provided a biosynthetic, immunomodulating lipid polysaccharide compound of formula (I)

(I)

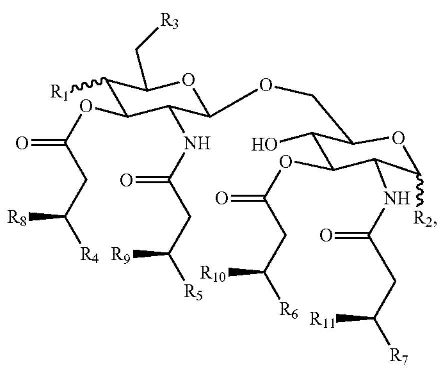

wherein $R_1$ and $R_2$ may be H, OH, protonated phosphate, a phosphate salt, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons, and $R_8$, $R_9$, $R_{10}$ and $R_{11}$ may be H, OH, or an alkyl or alkenyl ester of up to 18 carbons.

In one embodiment, there is a method of enhancing an immune response in a subject, comprising administering to the subject an effective amount of an immunogenic compound of formula (I)

(I)

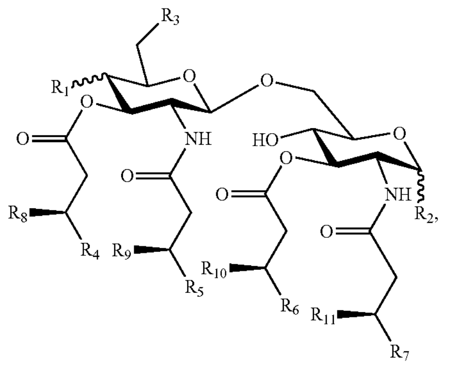

wherein $R_1$ and $R_2$ may be H, OH, protonated phosphate, a phosphate salt, a sugar phosphate, or a mono-, di- or poly-saccharide, $R_3$ may be OH or a mono-, di- or poly-saccharide, $R_4$, $R_5$, $R_6$ and $R_7$ may be an alkyl or alkenyl chain of up to 13 carbons, and $R_8$, $R_9$, $R_{10}$ and $R_{11}$ may be H, OH, or an alkyl or alkenyl ester of up to 16 carbons.

In some embodiments, a biosynthetic, immunomodulating lipid polysaccharide compound is at least one of:

(II)

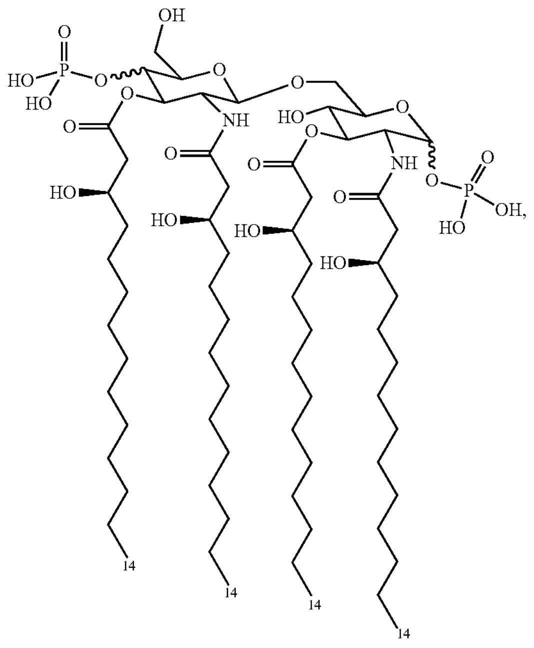

-continued
(III)
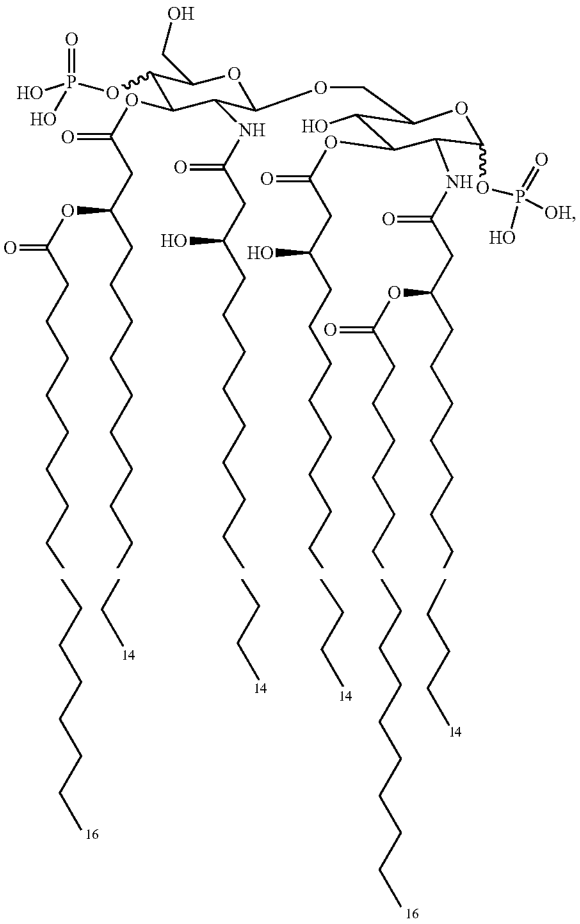
(IV)
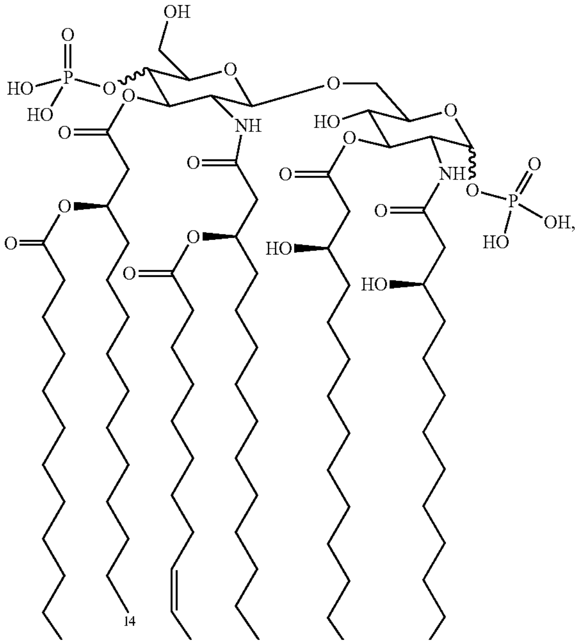
-continued
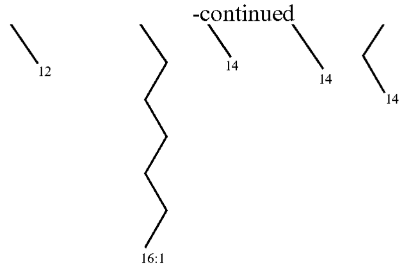
(V)
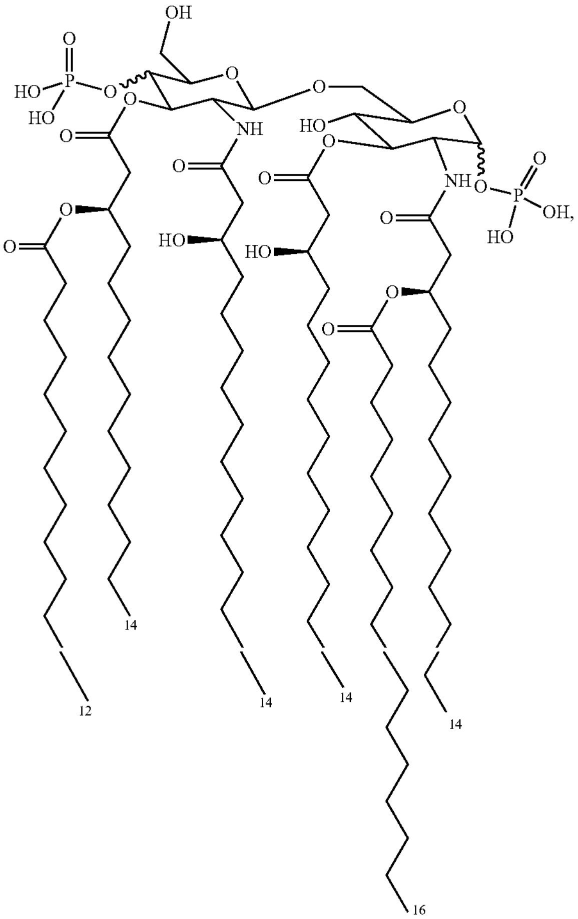

-continued
(VI)
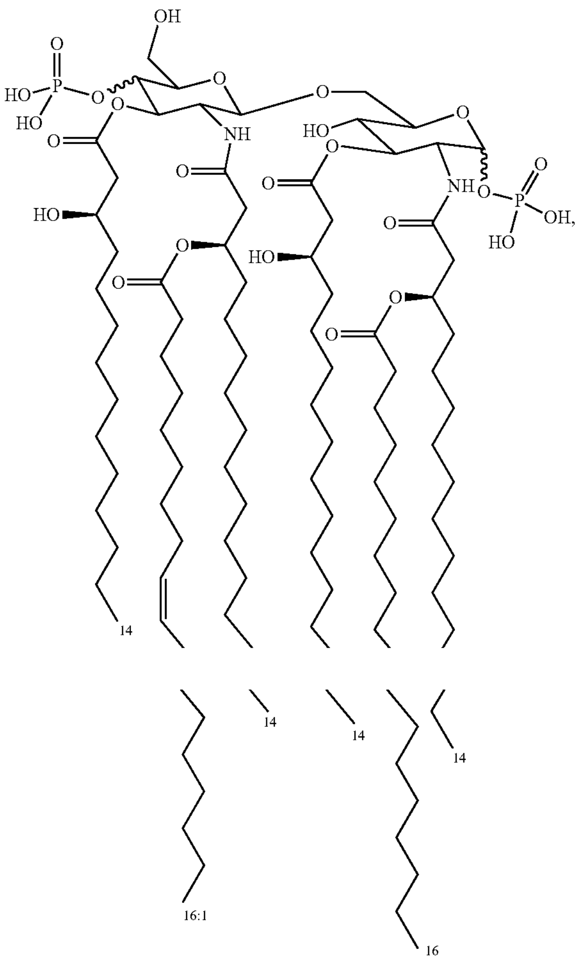
(VII)
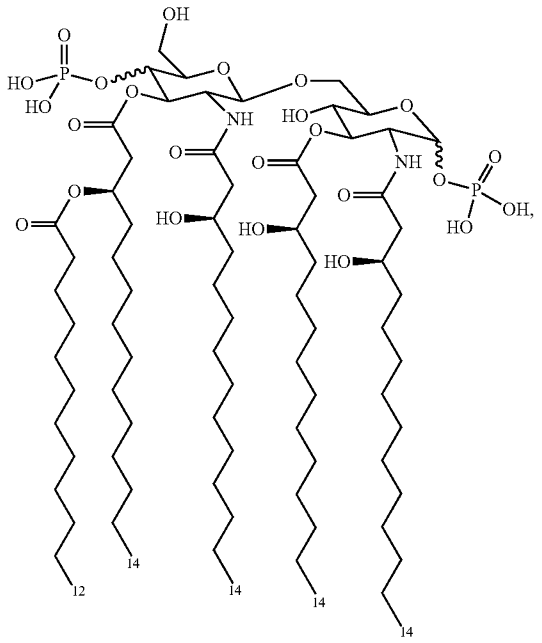
-continued
(VIII)
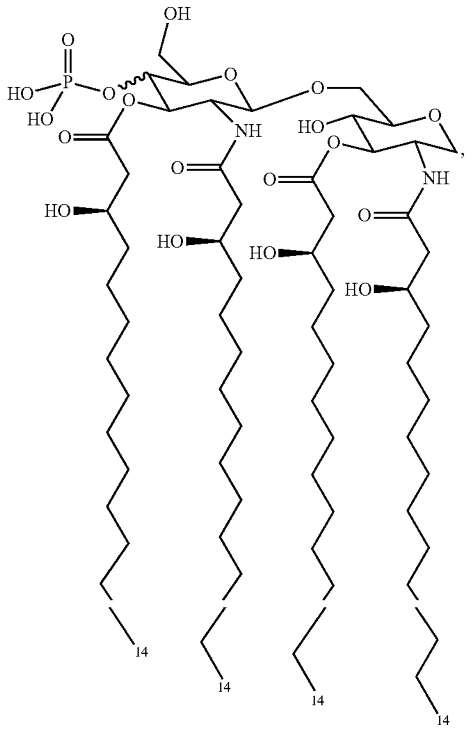
(IX)
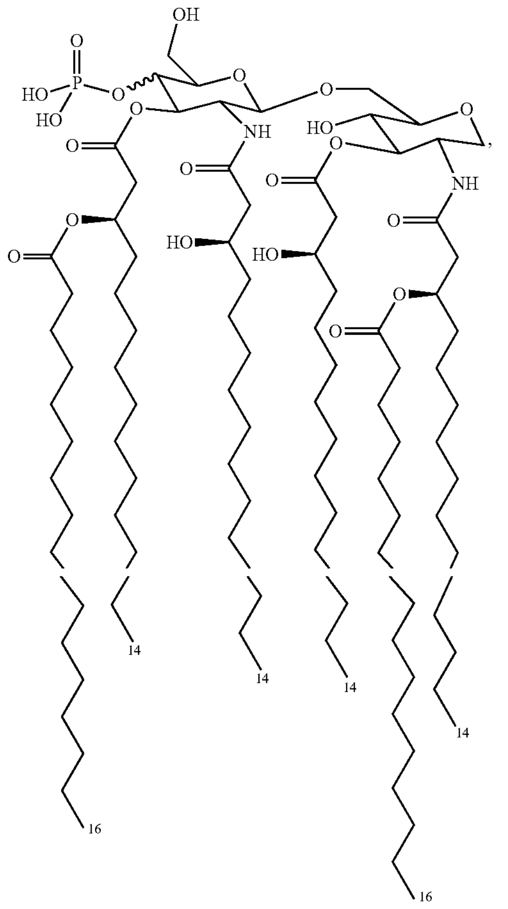

-continued
(X)
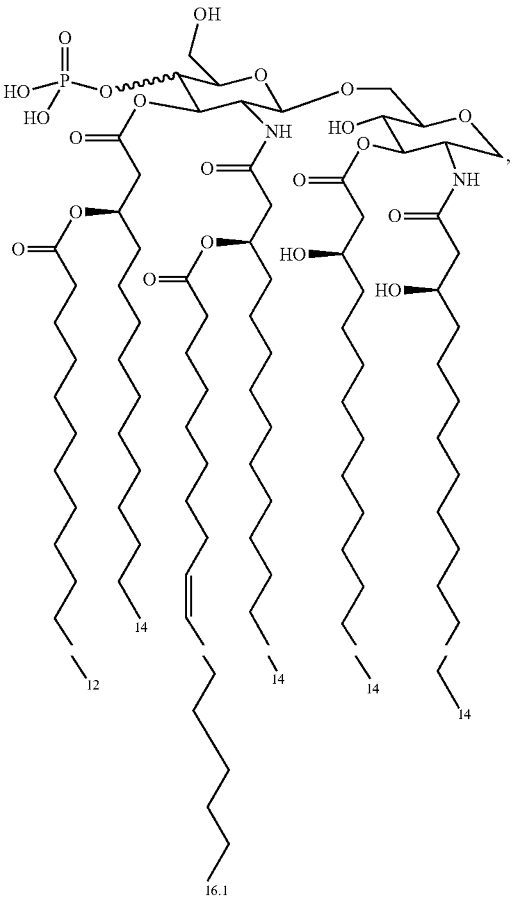
(XI)
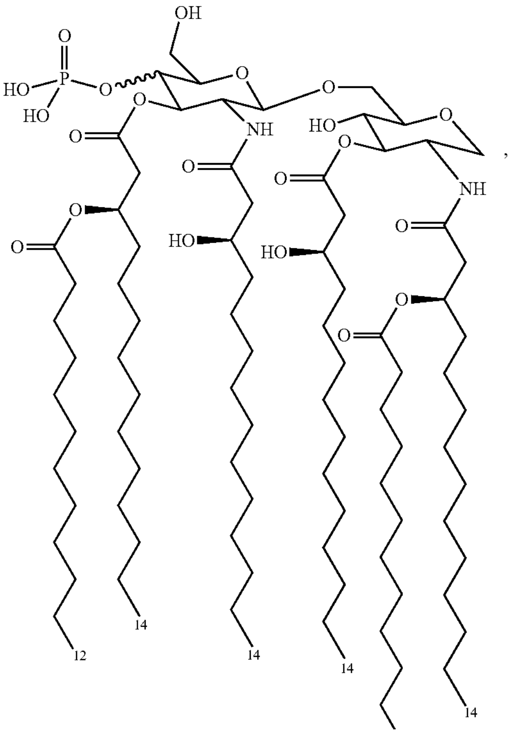
-continued
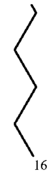
(XII)
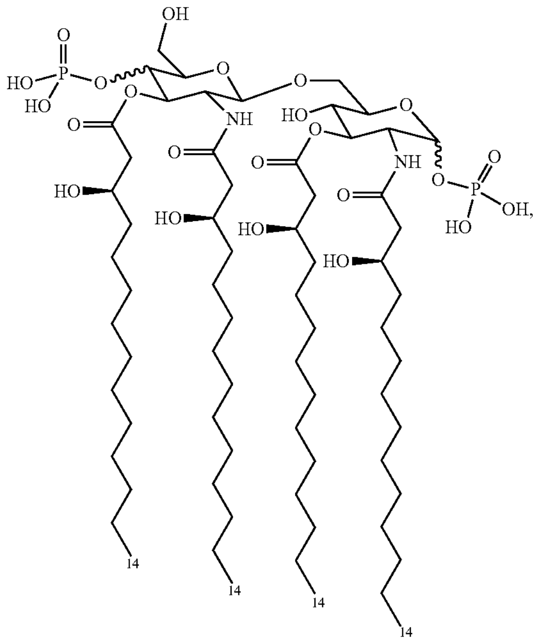
(XIII)
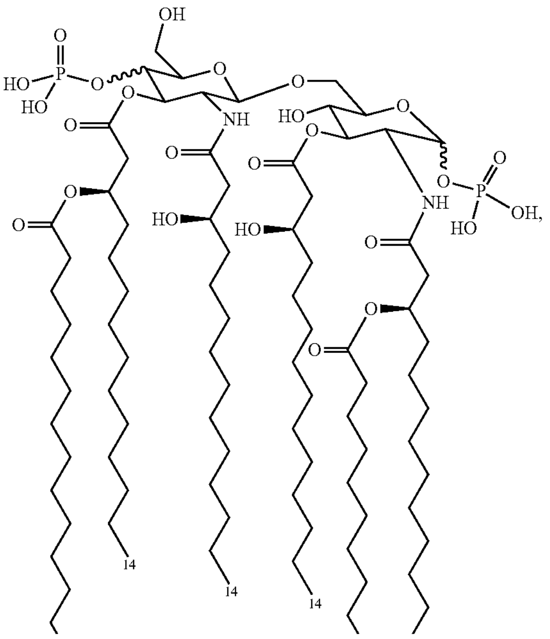

-continued

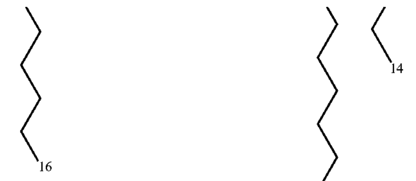

(XIV)

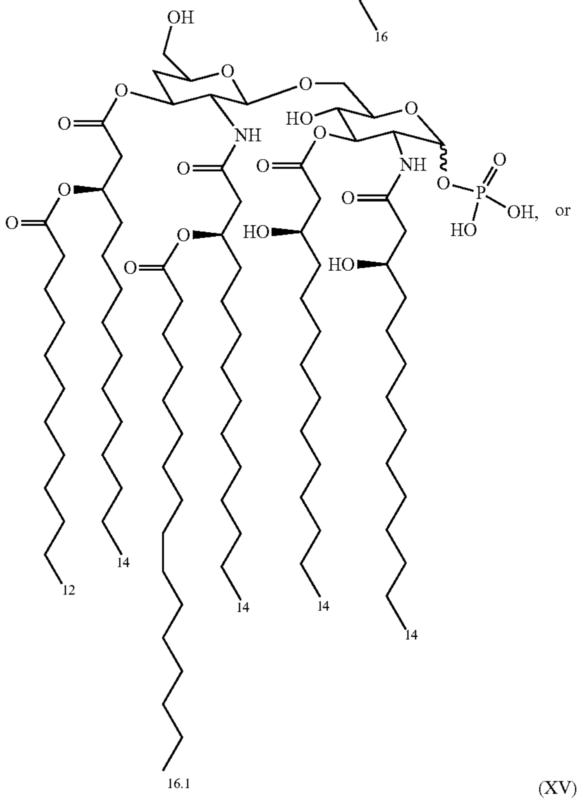

or (XV)

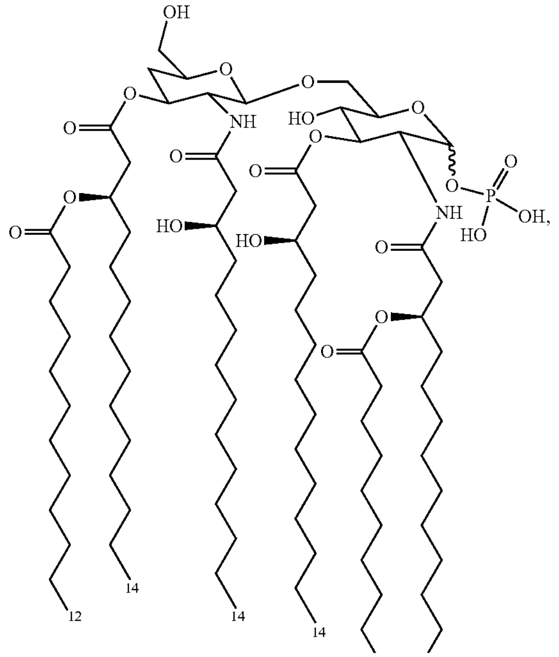

-continued

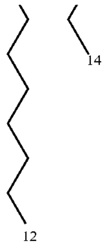

where the integers adjacent to fatty acid chains represent the number of carbons atoms in the respective fatty acid chain, and the ratios adjacent to fatty acid chains represent the number of carbons atoms in the respective fatty acid chain and the number of olefins within the fatty acid chain.

In particular embodiments, there is a kit, comprising one or more compositions of the disclosure. In specific embodiments, the kit further comprising one or both of an antigen and a pharmaceutically acceptable carrier.

It should be understood that the specific compositions and methods described herein are included by way of example and should not be understood as limiting. In consideration of the teachings herein, one having ordinary skill in the art would be able to develop additional compounds and methods of interest. Such compounds do not deviate from the overall spirit and therefore should be considered part of this invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

(FIG. 4A), AGP (FIG. 4D), and MPL (FIG. 4E). Structures in FIG. 4B and FIG. 4C have been modified through in trans BECC expression of the acyltransferases—PagP, MsbB, and LpxP. TLR4 mimetics (FIG. 4D) aminoalkyl glucosaminide phosphates (AGP), pink star indicates 1 position phosphate moiety is replaced by carboxylic acid and (FIG. 4E) monophosphorylated lipid A (MPL)—GSK, blue bracket represent heterogeneity of fatty acid number from 3-7 fatty acids present on glucosamine backbone and green star indicates removal of 1 position phosphate moiety in the GSK MPL preparations. Note: Avanti MPL is a synthetically derived hexa-acylated lipid A with all fatty acids 14 carbons in length. Lipid A modifications in these strains (FIGS. 4A-4C) have been confirmed by MS and GC analysis.

FIG. 8 provides a description and heterologous sources of LOS/Lipid A modifying enzymes for BECC, illustrating examples of modifying enzymes that may be used to generate *Y. pestis* or other strains with modified LOS.

FIG. 9 provides a description of individual strains generated, structure of the resultant lipid A, and mass at 37° C.

FIG. 10 provides description of individual strains generated, structure of the resultant lipid A, and mass when the *Y. pestis* strain was grown at 26° C.

FIG. 11 shows proinflammatory responses of specific glycolipid structures—Human cell lines when the *Y. pestis* strain was grown at 37° C. N/A: not available.

FIG. 12 provides proinflammatory responses of specific glycolipid structures—Human cell lines when the *Y. pestis* strain was grown at 26° C.

FIG. 13 demonstrates the structure of exemplary LPS molecules generated by methods of the disclosure.

FIG. 14 demonstrates the structure of exemplary LPS molecules generated by methods of the disclosure.

FIG. 15 demonstrates the structure of exemplary LPS molecules generated by methods of the disclosure.

FIG. 16 demonstrates the structure of exemplary LPS molecules generated by methods of the disclosure.

FIG. 17 demonstrates the structure of exemplary LPS molecules generated by methods of the disclosure.

FIG. 18 demonstrates the structure of exemplary LPS molecules generated by methods of the disclosure.

FIG. 19 demonstrates the structure of exemplary LPS molecules generated by methods of the disclosure.

FIG. 21 illustrates the structure of Control LPS molecules.

DETAILED DESCRIPTION OF THE INVENTION

Figure 1:
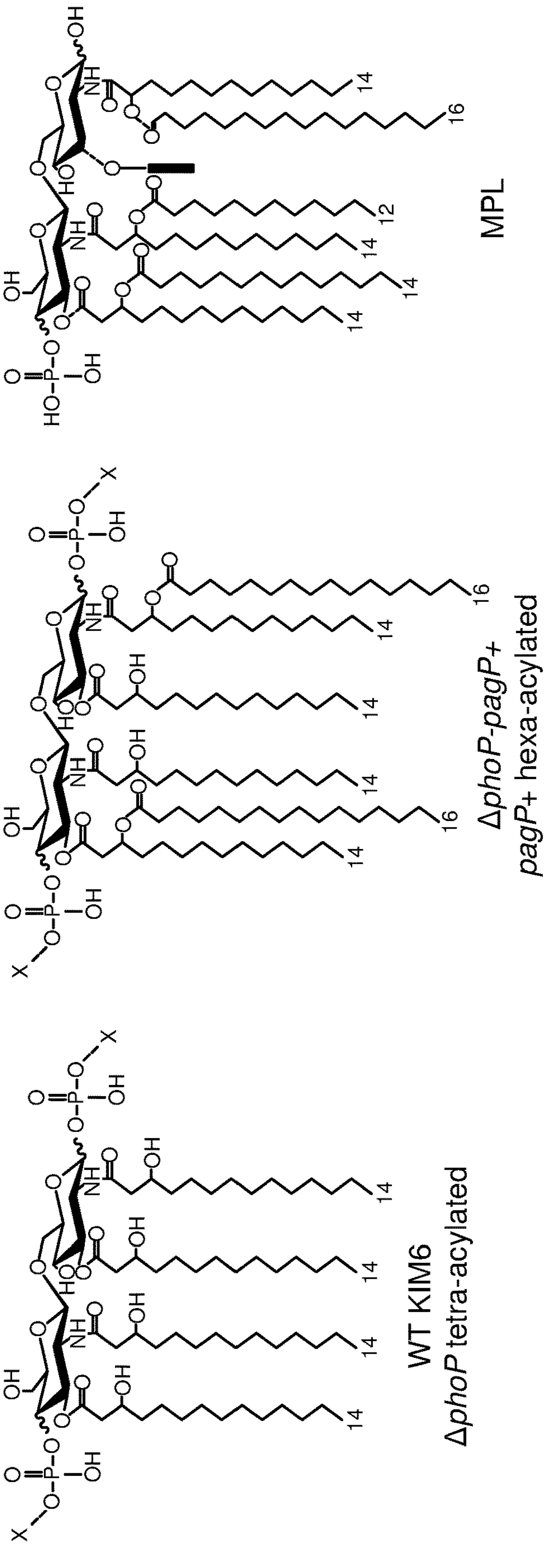
FIG. 1 shows representative Yp-based lipid A structures generated using BECC, as compared to WT grown at 37° C. (mammalian host temperature). X-potential addition site for aminoarabinose. —O—▬ Presence or absence of a 3-OH C14 fatty acid representing microheterogeneity of 3 position fatty acid group due to hydrolysis of LPS during MPL synthesis.

In keeping with long-standing patent law convention, the words "a" and "an" when used in the present specification in concert with the word comprising, including the claims, denote "one or more". Some embodiments may consist of or consist essentially of one or more elements, method steps, and/or methods of the disclosure. It is contemplated that any method or composition described herein can be implemented with respect to any other method or composition described herein embodiments that are disclosed and still obtain a like or similar result without departing from the spirit and scope of the subject matter.

The term "lipooligosaccharide/lipid A mimetic" as used herein refers to compound(s) that act on Toll-like receptor 4 (TLR4) and have immunomodulatory effects when used both as vaccine adjuvants or as stand-alone products.

Most vaccines contain adjuvants to help stimulate the production of immunity against the antigens or to stabilize antigen formulations to increase immune composition efficacy, including vaccine efficacy. Currently, there are few adjuvants licensed for use in human vaccines. These include alum salts, oil in water emulsions, the chemically derived monophosphoryl lipid A (MPL), a non-toxic toll-like 4 (TLR4) agonist. A number of synthetic lipid A mimetics (aminoalkyl glucosaminide 4-phosphates—AGPs) are presently under evaluation in bacterial and viral animal infection models. However, because of the variable heterogeneity from the chemical hydrolysis of LPS for the production of MPL and the limitations and labor-intensive nature of synthesizing AGPs that more closely mimic the structure of lipid A, alternative technologies are required for identifying novel adjuvants.

I. General Embodiments

Embodiments of the disclosure include lipooligosaccharide/lipid A-based mimetic compositions produced by bacteria for use in immunogenic compositions, such as for use as adjuvants, and the disclosure also includes methods of making and using the compositions. The compositions in certain aspects are lipid A mimetics, and they may be used alone as an immunogenic composition or with another immunogenic composition to elicit a desired immune response in an individual. In specific embodiments, the compositions are useful to block or arrest adverse in vivo immunological response, such as endotoxic shock by altering binding to TLR4. Embodiments include methods of generating the compositions, and further steps of the methods employ use of the compositions for administering to a mammal for eliciting an immune response.

In particular embodiments, this disclosure establishes processes for the synthesis and characterization of novel TLR4 mimetics with defined LOS/lipid A modifications utilizing novel bacterial enzymatic combinatorial chemistries (BECC) that will be useful to "fine tune" the balance between activating immunity while avoiding excessive adverse host reactions, such as inflammation. The in vitro and in vivo studies described herein establish a novel mechanism for adjuvant/vaccine design leading to well-defined, cell-type specific adjuvants that can target host cell-mediated responses plus robust antibody production. Ultimately, the future of vaccinology, particularly with regards to intractable infections and insufficient vaccine protection, is fundamentally linked to the development of safe, efficacious, and reliable adjuvants, and the present disclosure addresses this need.

Generation of novel, rationally-designed adjuvants normally requires the multidisciplinary effort in the fields of immunology, biochemistry, microbiology, and pharmacology, and the process of chemically deriving or synthesizing these molecules is expensive, labor intensive, and complex. In an aspect of this disclosure, one can "harness" the normal bacterial lipid A biosynthesis pathways present in all Gram-negative bacteria to synthesize structures based on the presence or absence of specific phosphate, acyl, and carbohydrate groups (for example). These structures can be produced efficiently, rapidly, and in sufficient quantities for use as stand-alone immunotherapeutic molecules or adjuvants in new immunogenic compositions, including vaccine formulations, for example. Thus, the bacteria utilized in the methods of the disclosure act as factories to supersede the extensive multidisciplinary efforts normally used to synthesize desired adjuvant molecules.

II. Exemplary Adjuvant Compositions

In particular embodiments, one or more adjuvant compositions are disclosed herein. One or more adjuvant compositions may be generated by methods of the invention, although one or more adjuvant compositions may be generated by other means and are used in methods of use in the disclosure, or one or more adjuvant compositions may be present in nature and are used in methods of use in the disclosure. The compositions may be provided to an individual in need thereof in an effective amount to produce an immune response in the individual that is potent, but not cytotoxic.

In certain embodiments of the disclosure, lipooligosaccharides comprising an oligosaccharide core with covalently-attached fatty acid chains are provided. The oligosaccharide sugars may be linked through O-, N-, S- or C-glycosidic bonds. The glycosidic bonds may be (1-4') or (1-6'), α- or β-glycosidic bonds. In particular embodiments, the lipooligosaccharides comprise a β(1-6')-D-glucosamine disaccharide core. The oligosaccharide sugars may be D-sugars, L-sugars, or a mixture thereof. In some embodiments, the covalently-attached fatty acid chains are alkyl fatty acids. In other embodiments, covalently-attached fatty acid chains may include at least one olefin, which may be a cis- or trans-olefin, or a mixture thereof, and/or at least one hydroxyl group. In certain aspects, a fatty acid chain may be covalently attached to the fatty acid hydroxyl group. The fatty acid chains may comprise continuous carbon chains of up to 18 carbon atoms. More preferable fatty acids comprise continuous carbon chains of 12, 14 or 16 carbon atoms. The fatty acid chains may be covalently attached to the oligosaccharide core through a variety of chemical bonds, including, but not limited to, ester, amide and thioester bonds. The modified lipooligosaccharides may include at least one phosphate group or sugar-phosphate ester. A carbon atom bearing a phosphate group or sugar-phosphate ester may be in an R or S stereochemical configuration. The sugar-phosphate ester may comprise a mono-, di- or poly-saccharide covalently attached to the phosphate group.

Thus, particular compositions of the disclosure comprise multiple moieties, and one or more of the moieties may be modifiable, including modifiable methods of the disclosure. In particular embodiments, the compositions comprise at least a sugar moiety, a phosphate moiety and a fatty acid moiety. Compositions of the disclosure may differ in one or more of the moieties.

A. Sugar Moiety(ies)

In specific embodiments, the compositions comprise one or more sugar units with attached acyl chains. In certain aspects, the compositions comprise a disaccharide. Although in Lipid A the sugars contain one phosphate group on each sugar, the lipid A mimetics of the disclosure may contain more than one or two phosphate group or no phosphate groups. In specific cases, the compositions comprise one, two, or three sugars, although more sugars may be included. The sugars may be of any kind, but in specific embodiments the simple sugars are glucose, galactose, arabinose, fructose, ribose, or the aminosugars are aminoarabinose, glucosamine, galactosamine, and so forth. In particular embodiments, the sugars have a linkage group to the fatty acids, such as an amine group, ketone group, and so forth.

B. Phosphate Moiety(ies)

In particular embodiments, the compositions comprise at least one phosphate, including one phosphate, two phosphates, or three or more phosphates. Each sugar in the molecule may have one or more phosphates. Each phosphate in the composition may be unmodified or may be modified to have attached thereto another group, such as another sugar as defined above or ethanolamine.

C. Fatty Acid Moiety(ies)

In certain embodiments, the compositions comprise at least one fatty acid moiety. In some cases the compositions comprise one, two, three, four, five, six or more fatty acids. In particular embodiments, no more than eight fatty acids are included in the compositions. The length of one or more of the fatty acid chains may be an aspect for modification. In specific cases all of the fatty acids are of the same length, whereas in other cases the fatty acids may be of different lengths. In certain molecules, all but one fatty acid are of the same length. In specific embodiments, one or more fatty acids are up to twenty-two carbons in length. Specifically, the fatty acids may be 10, 12, 14, 16, 18, 20, 22, or more carbons in length. In particular embodiments, the fatty acids have at least one double bond, including one double bond, two double bonds, three double bonds, and so forth.

III. Extraction of Lipooligosaccharide/Lipid A-Based Mimetics

Upon production of the lipooligosaccharide/lipid A-based mimetics in the selected bacterial strain, the lipooligosaccharide/lipid A-based mimetics are obtained from the bacteria. The mimetic molecules may be obtained by any suitable method, but in specific embodiments they are chemically extracted using standard LOS extraction protocols. In specific cases, initially multiple types of LOS extraction procedures are employed to obtain LOS from the bacteria, and extraction procedures may be performed more than once. In particular aspects, the extraction procedures are phenol-based, magnesium-precipitation-based, ammonium hydroxide/isobutyric acid-based, chloroform-methanol-based, detergent-based, and so forth.

Once the LOS preparation is obtained from the bacteria, the lipid A fraction is liberated using gentle hydrolysis to protect sensitive structural elements.

In particular embodiments, lipid A or its mimetics may be isolated as follows. Lipid A was isolated after hydrolysis in 1% SDS at pH 4.5. Briefly, 500 μl of 1% SDS in 10 mM Na-acetate (pH 4.5) was added to a lyophilized sample. Samples were incubated at 100° C. for 1 h, frozen, and lyophilized. The dried pellets were resuspended in 100 μl of water and 1 ml of acidified ethanol (100 μl 4 N HCl in 20 ml 95% ethanol). Samples were centrifuged at 5,000 rpm for 5 min. The lipid A pellet was further washed (three times) in 1 ml of 95% ethanol. The entire series of washes was repeated twice. Samples were resuspended in 500 μl of water, frozen on dry ice, and lyophilized. Lipid A was used for matrix-assisted laser desorption ionization (MALDI) mass spectrometry analysis.

IV. Analysis of Exemplary Lipooligosaccharide/Lipid A-based Mimetic Compositions Following extraction of the desired lipooligosaccharide/lipid A-based mimetic, the mimetic is analyzed for structure and/or function. In certain cases, the structure is analyzed prior to the function, whereas in other cases the function is analyzed prior to the structure. The analysis may be on a small scale with only a few mimetics being analyzed at substantially the same time or on a large scale with many mimetics being analyzed at substantially the same time.

In some cases, the structure is analyzed by routine methods in the art, including using one or more procedures for the analysis. In particular embodiments, mass spectrometry, gas chromatography, or both are utilized for analysis of structure. For mass spectrometry embodiments, matrix-assisted laser desorption/ionization/time-of-flight mass spectrometry (MALDI-TOF) and electrospray ionization (ESI) are utilized, including in both the negative and positive-ion mode. Other steps to analyze LOS/lipid A fatty acid content can include acid hydrolysis, methylation, and hexane extraction.

In specific embodiments, one or more structures produced by methods of the disclosure are analyzed as follows.

V. Electrospray Ionization Linear Ion Trap Fourier Transform Ion Cyclotron Resonance Mass Spectrometry Lipid A was analyzed by ESI in the negative mode of an LTQ-FT linear ion trap Fourier transform ion cyclotron resonance mass spectrometer (Thermo Fisher). Samples were diluted to ~0.3-1.0 mg/ml in chloroform/methanol (1:1) and infused at a rate of 0.5-1.0 ul/min via a fused silica capillary (75 um i.d./360 um o.d.) with an ~15 um spray tip (New Objective). Instrument calibration and tuning parameters were optimized by using a solution of Ultramark 1621 (Lancaster Pharmaceuticals). For experiment acquired in the ICR cell, resolution was set at 100K and ion populations were held constant by automatic gain control at $1.0\times10^6$ and $5.0\times10^5$ for MS and MS/MS, respectively. For tandem mass spectra, the precursor ion selection window was set to 4-8 DS and the collision energy was set to 30% on the instrument scale. The CID MS' analysis in the linear ion trap was acquired with an ion population of $1.0\times10^4$ maximum fill time of 200 ms. The subsequent $MS^3$ and $MS^4$ had an isolation window of 2 Da with a collision energy of 25%. All spectra were acquired over a period of 1-2 min and averaged. Typically, MS and $MS^2$ events were mass analyzed in the ICR cell, and the $MS^3$ and $MS^4$ were mass analyzed in the LTQ. Infrared multiphoton dissociation (IRMPD) $MS^2$events were acquired in the ICR cell using similar detection parameters to those described above. Precursor ions were irradiated by IR photons produced by a $CO_2$ laser [Synrad firestar Series V20), Model FSV20SFB; 75 W (10.2-10.8 um)] with pulse durations of 20-100 ms and pulse power of 20-80%. Data were acquired and processed with Xcaliber (version 1.4; Thermo Fisher) using seven-point Gaussian smoothing. On-line liquid chromatography ESI tandem MS experiments were performed by interfacing a custom-fabricated microcolumn (fused-silica capillary) packed with silica to the LTQ-FTESI source.

VI. Electrospray Ionization Tandem Quadrupole Mass Spectrometry

Lipid A was analyzed by ESI in the negative ion mode on a Sciex API III tandem quadrupole mass spectrometer (Perkin Elmer). Samples were diluted to ~0.3-1.0 mg/ml in chloroform/methanol (1:1) and infused at a rate of 0.5-1.0 ul/min via a fused silica capillary (i.d. 100 um) by using a syringe pump (Harvard Apparatus Model 11). The instrument was operated with the following settings: needle voltage, −4300 V; counter electrode, −650 V, nebulizer gas pressure, 20 psi; curtain gas pressure, 10 psi; declustering potential, −35 V; collision cell entrance potential, −10 V; collision cell exit potential, −15V; and collision gas, argon. Tandem MS data were acquired in both product and precursor ion scan modes.

VI. MALDI-TOF MS Analysis

Lipid A structures were assessed by negative-ion MALDI-TOF MS. Lyophilized lipid A was extracted in chloroform/methanol and then 1 μl was mixed with 1 μl of Norharmane MALDI matrix. All MALDI-TOF experiments were performed using a Bruker Autoflex Speed MALDI-TOF mass spectrometer (Bruker Daltonics, Billerica, Mass.). Each spectrum was an average of 300 shots. ES tuning mix (Aligent, Palo Alto, Calif.) was used for calibration.

VII. Gas Chromatography

LPS fatty acids were converted to fatty acid methyl esters and analyzed by gas chromatography (GC) essentially as previously described (ref). Briefly, 10 mg of lyophilized bacterial cell pellet was incubated at 70° C. for 1 hour in 500 μl of 90% phenol and 500 μl of water. Samples were then cooled on ice for 5 minutes and centrifuged at 10,000 rpm for 10 minutes. The aqueous layer was collected and 500 μl of water was added to the lower (organic) layer and incubated again. This process was repeated twice more and all aqueous layers were pooled. Two ml of ethyl ether was added to the harvested aqueous layers, this mixture was then vortexed and centrifuged at 3,000 rpm for 5 minutes. The lower (organic) phase was then collected and 2 ml of ether were added back remaining aqueous phase. This process was carried out twice more. The collected organic layer was then frozen and lyophilized overnight. LPS fatty acids were converted to fatty methyl esters, in the presence of 10 μg pentadeconic acid (Sigma, St Louis, Mo.) as an internal standard, with 2 M methanolic HCl (Alltech, Lexington, Ky.) at 90° C. for 18 hours.

Functional analysis of the lipid A mimetic structures may be performed by standard methods in the art to ascertain immune function of the mimetics. In vitro analysis methods may be preceded by in vivo analysis methods. In at least some cases, output of the methods for the particular mimetic is compared to a reference, such as MPL, for example. Those mimetic compositions having suitable immune function may be utilized as an adjuvant. In specific aspects, the desired molecule has low toxicity yet is immunostimulatory as shown, for example, by triggering chemotaxis without profound apoptosis or pyroptosis. Examples of in vitro methods to analyze the function of the molecules includes at least an in vitro cell stimulation assay, and a range of doses of the particular lipid A mimetic being tested may be screened. The cells for the cell stimulation may be of a human monocytic cell line, for example. The stimulation of the cells may be measured by assaying for certain cytokines (such as IL-8) and by assaying for RANTES (regulated on activation, normal T cell expressed and secreted), which is a chemokine. Those candidate molecules that show utility in the in vitro aspects may be tested in the in vivo assays. The candidate lipooligosaccharide/lipid A-based mimetics may be assayed by in vivo models, such as in vivo murine screening models. In specific aspects, the candidate molecules are provided to mice alone and with known immunogenic reagents to probe innate and adaptive immune potentiation; in certain aspects, direct modulation of cell mediated and humoral immunity and balancing of $Th_1/Th_2$ responses are examined.

In specific embodiments, the function of the compositions may be assayed as follows.

Primary screening will be performed for all new molecules in systemic and airway mouse and human macrophage cell lines (RAW, THP-1, MH-S, U937, respectively) over a wide dose range. Supernatants from cell stimulations will be screened by cytokine multiplex assays for inflammatory markers of macrophage activation, including IL-1β. Primary screening will be performed for all new molecules in systemic and airway mouse and human macrophage cell lines (RAW, THP-1, MH-S, U937, respectively) over a wide dose range. Supernatants from cell stimulations will be screened by cytokine multipleest for development of an adjuvant molecule include down-modulated inflammatory cytokine profiles (low IL-8) and up-regulated T cell fate-determining cytokines, such as IL-12 (promotes $T_H1$) and IL-23p19 (promotes $T_H17$). Tertiary screening will verify TLR4-mediated activity of the candidate molecules using human and mouse TLR4-transfected HEK cells with an inflammatory activation (NF-κB). Tertiary screening will verify TLR4-mediated activity of the candidate molecules using human and mouse TLR4-transfected HEK cells with an inflammatory activation (NF-se range. Supernatants from cell stimulations will be screened by cytokine multiple BECC-synthesized TAMs, immature DCs from mouse and human (BMDC, PBMC) will be stimulated and analyzed for maturation (CD83) and activation (CD86, MHCII, etc.) surface markers by flow cytometry.

Finally, ten candidates will be identified from the outlined in vitro screening to advance to an in vivo screening for acute toxicity. C57BL/6 mice (n=5 per group) will receive a single, intraperitoneal (IP) dose of a candidate molecule. Animals will be monitored closely for clinical signs of acute toxicity and/or a lethal inflammatory response including loss of weight, core temperature dysregulation, and behavioral changes. Sera will be collected and assayed for unacceptably high circulating endotoxemia markers (TNF-α). Sera will be collected and assayed for unacceptably high circulati:creatinine ratio, ALT, AST, IRN, total protein) 1-7 days post-injection.

In particular embodiments, compositions of the disclosure are assayed in challenge studies. The specific challenge models employed will be those that will differentiate between candidate compound outcomes. As examples, the *S. aureus* dermonecrosis model for the generation of high-affinity anti-A-T mAbs may be employed. Here, mice are immunized 3× biweekly via the intramuscular route, then intradermally challenged with a dose of *S. aureus* calibrated to induce non-healing dermal lesion. Monitoring of lesion size are conducted in vaccinated mice, and skin biopsies are analyzed for presence of cytokines, bacterial load, and infiltrating leukocytes. Alternatively, a Respiratory syncytial virus (RSV) infection model in mice may be utilized if candidate compounds demonstrate superior capability in the induction of RSV-neutralizing Abs and T cell responses.

VIII. Use of Exemplary Lipooligosaccharide/Lipid A-Based Mimetic Compositions The compositions of the present disclosure may be used for medicinal purposes of any kind, but in specific embodiments, the lipid A mimetic compositions are employed as an immunogenic composition alone or as part of an immunogenic composition having at least one component other than the lipid A mimetic. The immunogenic composition may be an adjuvant, for example. Adjuvants are useful because they reduce the amount of the active component required in an immunogenic composition, they may allow the use of fewer doses of the immunogenic composition because the immune response is stronger and lasts longer, and those with compromised immune systems benefit from them because their immune system requires an extra boost to provide protection.

In particular cases, more than one lipid A mimetic is employed in an immunogenic composition, including two, three, or more lipid A mimetics. The lipid A mimetic may be formulated for use as an immunogenic composition, including having an appropriate carrier excipient. A therapeutically effective amount of the composition(s) is employed, and the proper amount may be determined by any suitable method in the art. The immunogenic composition may be delivered to the individual by any appropriate means, including by injection or orally. Multiple deliveries of the lipooligosaccharide/lipid A-based mimetic(s) may be employed.

The delivery of the lipid A mimetic in an immunogenic composition may occur prior to exposure of the individual to a pathogen and/or following exposure of the individual to a pathogen. In some cases, the lipid A mimetic-comprising immunogenic composition is given to an individual as part of a routine medical practice in preventative measures. In certain cases, the lipid A mimetic immunogenic composition is delivered to an individual in anticipation of exposure to a pathogen or in anticipation of being at risk for exposure to a pathogen. In some cases, the immunogenic composition is provided to an individual not for use with a pathogen, but instead is used for another medical condition, such as for cancer or inflammation-mediated coronary heart disease, for example. Thus, the immunogenic composition may be prophylactic or therapeutic.

In some cases, the lipid A mimetic composition is employed for immune stimulation for a pathogen, such as any bacteria or virus. However, in specific embodiments, the immunogenic composition of the disclosure is useful for measles, rubella, mumps, yellow fever, typhoid fever, smallpox, polio, tuberculosis, plague, chickenpox, human papilloma virus (HPV), influenza, *Haemophilus influenzae* type B, rotavirus, pneumonia, hepatitis A, hepatitis B, hepatitis C, diphtheria, pertussis, tetanus, meningococcal, West Nile Virus, Dengue, Japanese encephalitis virus, Chikungunya, HIV, tularemia, salmonellosis, listeriosis, and/or *Shigella*. The lipid A mimetic immunogenic compositions may be applied to mammals other than humans, such as dogs, cats, horses, cows, pigs, sheep, and so forth. For example, a dog may be given an immunogenic composition comprising a lipid A mimetic of the disclosure, such as an immunogenic composition for canine distemper, canine parvovirus, infectious canine hepatitis, adenovirus-2, leptospirosis, *Bordetella*, canine parainfluenza virus, and Lyme disease, for example.

In some cases, a lipid A mimetic(s)-comprising immunogenic composition comprises a plurality of antigenic compositions each suitable for a different pathogens, thereby being prophylactic for more than one pathogen. In such cases, one or more lipid A mimetics may be employed.

VIX. Vaccines and Immunogenic Compositions Generally

Embodiments of the disclosure employ lipooligosaccharide/lipid A-based mimetics as adjuvants either alone or with another immunogenic composition. In some embodiments, the immunogenic composition to be employed with the lipooligosaccharide/lipid A composition is a vaccine. The immunogenic composition (which may be referred to as an adjuvantic composition of the disclosure may be considered an antigenic composition. For an immunogenic composition to be useful, it must induce an immune response to the antigen in a cell, tissue or animal (e.g., a human). As used herein, an "antigenic composition" may comprise an antigen (e.g., a peptide, polypeptide, weakened microbe, a killed microbe, one or more antigens, a toxoid, polysaccharide, or nucleic acid), a nucleic acid encoding an antigen (e.g., an antigen expression vector), or a cell expressing or presenting an antigen. In other embodiments, the immunogenic composition is in a mixture that comprises an additional immunostimulatory agent or nucleic acids encoding such an agent. Immunostimulatory agents include but are not limited to an additional antigen, an immunomodulator, an antigen presenting cell, or an adjuvant that is other than the lipid A mimetics of the disclosure. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In certain embodiments, an antigenic composition or immunologically functional equivalent comprising the lipid A mimetic of the disclosure may be used as an effective vaccine in inducing a humoral and/or cell-mediated immune response in an animal. The present disclosure contemplates using a lipid A mimetic in one or more immunogenic compositions or vaccines for use in both active and passive immunization embodiments.

In some cases, one or more immunogenic composition components may be comprised in a lipid or liposome. In another non-limiting example, the immunogenic composition may comprise one or more adjuvants. An immunogenic composition may be prepared and/or administered by any method disclosed herein or as would be known to one of ordinary skill in the art, in light of the present disclosure.

The type of antigens that may be employed with one or more lipid A mimetics of the disclosure may be of any kind, including a proteinaceous antigen that may be produced by chemical synthesis or expression from a nucleic acid sequence, for example. Proteinaceous antigens may comprise a peptide or polypeptide. Another type of antigen in which a lipid A mimetic is used as an adjuvant includes genetic antigens, wherein an immune response may be promoted by transfecting or inoculating an animal with a nucleic acid encoding an antigen, following which one or more cells comprised within a target animal then expresses the sequences encoded by the nucleic acid after administration of the nucleic acid to the animal; the antigen may also be in the form, for example, of a nucleic acid (e.g., a cDNA or an RNA) encoding all or part of the peptide or polypeptide sequence of an antigen. Expression in vivo by the nucleic acid may be, for example, by a plasmid type vector, a viral vector, or a viral/plasmid construct vector. In yet another case, a lipid A mimetic is employed with a cellular antigen comprising a cell expressing the antigen, such as a cell isolated from a culture, tissue, organ or organism. The cell may be transfected with a nucleic acid encoding an antigen to enhance its expression of the antigen. Of course, the cell may also express one or more additional components, such as immunomodulators or adjuvants (other than the lipid A mimetic adjuvant). An immunogenic composition may comprise all or part of the cell.

It is contemplated that an antigenic composition includes the antigen and the lipooligosaccharide/lipid A-based mimetic(s), but there may also be one or more additional components to form a more effective antigenic composition. Non-limiting examples of additional components include, for example, one or more additional antigens, immunomodulators or adjuvants to stimulate an immune response to the antigenic composition.

For example, it is contemplated that immunomodulators can be included in the composition to augment a cell's or a patient's (e.g., an animal's) response. Immunomodulators can be included as purified proteins, nucleic acids encoding immunomodulators, and/or cells that express immunomodulators in the vaccine composition. In specific embodiments, various combinations of immunomodulators may be used (e.g., a cytokine and a chemokine). When cytokines are included in the compositions, they may be interleukins, cytokines, nucleic acids encoding interleukins or cytokines, and/or cells expressing such compounds are contemplated as possible vaccine components. Interleukins and cytokines include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, IL-22, IL-23 β-interferon, α-interferon, g-interferon, angiostatin, thrombospondin, endostatin, GM-CSF, G-CSF, M-CSF, METH-1, METH-2, tumor necrosis factor, TGFβ, LT and combinations thereof. In some cases, chemokines, nucleic acids that encode for chemokines, and/or cells that express such also may be used as components of the composition. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP1-alpha, MIP1-Beta, IP-10 and combinations thereof. The skilled artisan will recognize that certain cytokines are also known to have chemoattractant effects and could also be classified under the term chemokines. Other examples of molecules to include in the composition are immunogenic carrier proteins, such as hepatitis B surface antigen, keyhole limpet hemocyanin (KLH), bovine serum albumin (BSA), ovalbumin, mouse serum albumin or rabbit serum albumin. Biological response modifiers (BRM) may be utilized that have been shown to upregulate T cell immunity or downregulate suppressor cell activity. Such BRMs include, but are not limited to, cimetidine (CIM; 1200 mg/d) (Smith/Kline, PA); low-dose cyclophosphamide (CYP; 300 mg/$m^2$) (Johnson/Mead, NJ), or a gene encoding a protein involved in one or more immune helper functions, such as B-7.

In some aspects to the disclosure, an adjuvant in addition to the lipooligosaccharide/lipid A-based mimetic(s) is employed in an immunogenic composition. An example of an adjuvant is alum or squalene.

In one aspect, an adjuvant effect is achieved by use of an agent, such as alum, used in about 0.05 to about 0.1% solution in phosphate buffered saline. Alternatively, the antigen is made as an admixture with synthetic polymers of sugars (Carbopol®) used as an about 0.25% solution. Adjuvant effect may also be made my aggregation of the antigen in the composition by heat treatment. Some adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

In certain embodiments, hemocyanins and hemoerythrins may also be used in the invention. The use of hemocyanin from keyhole limpet (KLH) is preferred in certain embodiments, although other molluscan and arthropod hemocyanins and hemoerythrins may be employed. Various polysaccharide adjuvants may also be used. Polyamine varieties of polysaccharides are useful, such as chitin and chitosan, including deacylated chitin. Another group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

Another adjuvant contemplated for use in the present invention is BCG. BCG (*Bacillus* Calmette-Guerin, an attenuated strain of *Mycobacterium*) and BCG-cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., 1988). Trehalose dimycolate may be prepared as described in U.S. Pat. No. 4,579,945.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., 1994; Hunter et al., 1991) may also be employed. Oligonucleotides are another useful group of adjuvants (Yamamoto et al., 1988). Quil A and lentinen are other adjuvants that may be used in certain embodiments of the present invention. One group of adjuvants that are useful include detoxified endotoxins.

An antigenic composition of the present invention may be mixed with one or more additional components (e.g., excipients, salts, etc.) that are pharmaceutically acceptable and compatible with at least one active ingredient (e.g., antigen). Suitable excipients are, for example, water, saline, dextrose, glycerol, ethanol and combinations thereof. An antigenic composition of the present invention may be formulated as a neutral or salt form. A pharmaceutically-acceptable salt, includes the acid addition salts (formed with the free amino groups of the peptide) and those that are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2-ethylamino ethanol, histidine, procaine, and combinations thereof. In addition, if desired, an antigenic composition may comprise minor amounts of one or more auxiliary substances such as for example wetting or emulsifying agents, pH buffering agents, etc. which enhance the effectiveness of the antigenic composition or vaccine.

X. Vaccine and Immunogenic Composition Preparations

Once produced, synthesized and/or purified, an antigen or other vaccine component may be prepared as a vaccine or immunogenic composition for administration to an individual, wherein the vaccine or immunogenic composition comprises the lipooligosaccharide/lipid A-based mimetic. The preparation of a vaccine is generally well understood in the art, as exemplified by U.S. Pat. Nos. 4,608,251, 4,601,903, 4,599,231, 4,599,230, and 4,596,792, all incorporated herein by reference. Such methods may be used to prepare a vaccine or immunogenic composition comprising an antigen as active ingredient(s) and a lipooligosaccharide/lipid A-based mimetic(s), in light of the present disclosure. In particular embodiments, the compositions of the present invention are prepared to be pharmacologically acceptable.

Pharmaceutical compositions of the present invention comprise an effective amount of one or more lipooligosaccharide/lipid A-based mimetics dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The means of preparation of a pharmaceutical composition that contains at least one lipooligosaccharide/lipid A-based mimetics or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The compositions may comprise different types of carriers depending on whether it is to be administered in solid, liquid or aerosol form, and whether it need to be sterile for such routes of administration as injection. Except insofar as any conventional carrier is incompatible with the active ingredient, its use in the therapeutic or pharmaceutical compositions is contemplated.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the composition is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assailable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi.

It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

XI. Vaccine and Immunogenic Composition Administration

The manner of administration of a vaccine or immunogenic composition may be varied widely. Any of the conventional methods for administration of a vaccine or immunogenic composition are applicable. For example, a vaccine or immunogenic composition may be conventionally administered intravenously, intradermally, intraarterially, intraperitoneally, intralesionally, intracranially, intraarticularly, intraprostaticaly, intrapleurally, intratracheally, intranasally, intravitreally, intravaginally, intratumorally, intramuscularly, intraperitoneally, subcutaneously, intravesicularlly, mucosally, intrapericardially, orally, rectally, nasally, topically, in eye drops, locally, using aerosol, injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

An immunization schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

A vaccine or immunogenic composition is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., innoculations) are also variable, but are typified by an initial administration followed by subsequent inoculation(s) or other administration(s).

In many instances, it will be desirable to have multiple administrations of the vaccine or immunogenic composition, usually not exceeding six immunizations, more usually not exceeding four immunizations and in some cases one or more, usually at least about three immunizations. The immunizations will normally be at from two to twelve week intervals, more usually from three to five week intervals. Periodic boosters at intervals of 1-5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the antigen can be performed, following immunization.

Following use of the lipooligosaccharide/lipid A-based mimetic in an immunogenic composition in an individual, an immune response is enhanced. The enhanced immune response may be an active or a passive immune response.

XII. Kits

Any of the compositions described herein may be comprised in a kit. In a non-limiting example, one or more lipooligosaccharide/lipid A-based mimetics and/or bacterial strains to produce them and/or reagents for modifying the bacteria are comprised in a kit. In certain aspects, one or more reagents for modifying, culturing, and/or extracting from bacteria are include in the kit.

In specific embodiments, one or more lipooligosaccharide/lipid A-based mimetics are included in the kit and may or may not be formulated with another agent. The other agent may be an immunogenic composition itself, such as a vaccine, or it may be part of an immunogenic composition, such as an antibody, a weakened microbe, a killed microbe, one or more antigens, a toxoid, polysaccharide, or nucleic acid. The lipooligosaccharide/lipid A-based mimetics may be formulated for delivery to a mammal or may be provided with one or more reagents to produce a formulation for delivery to a mammal. The bacterial strain of the kit may be provided as a bacterial stab, bacterial slant, frozen glycerol stock, or freeze dried powder, as examples. The bacteria may be provided in the kit at a particular desired temperature, including between frozen (−80° C.) and room temperature. In embodiments, the kit comprises one or more reagents for modifying a bacteria, such as reagents to handle a recombinant vector and/or reagents to assay the bacteria for presence of the vector (such as PCR reagents, restriction enzymes, polymerases, ligases, buffers, nucleotides, etc.).

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there are more than one component in the kit, the kit also will generally contain a second, third or other additional container into which the additional components may be separately placed. However, various combinations of components may be comprised in a vial. The kits of the present invention also will typically include a means for containing the compositions in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. In some cases, the container means may itself be a syringe, pipette, and/or other such like apparatus, from which the formulation may be applied to a desired area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a container means for containing a sterile, pharmaceutically acceptable buffer and/or other diluent.

XIII. Exemplary Bacterial Strains

Embodiments of the disclosure employ Gram negative bacterial strains to produce a desired composition. The Gram negative bacteria may be of any kind, including from *Acetobacter, Borrelia, Bortadella, Burkholderia, Campylobacter, Chlamydia, Enterobacter, Eshcerichia, Fusobacterium, Helicobacter, Hemophilus, Klebsiella, Legionella, Leptospiria, Neisseria, Nitrobacter, Proteus, Pseudomonas, Ricketsia, Salmonella, Serratia, Shigella, Thiobacter, Treponema, Vibrio*, or *Yersinia*. In specific embodiments, one or more of the following bacteria are utilized in methods of the disclosure: Acetic acid bacteria, *Acinetobacter baumannii, Agrobacterium tumefaciens, Anaerobiospirillum, Arcobacter, Arcobacter skirrowii, Armatimonas rosea, Bacteroides, Bacteroides fragilis, Bacteroides ruber, Bartonella taylorii, Bdellovibrio, Brachyspira, Cardiobacterium hominis, Chthonomonas calidirosea, Coxiella burnetii, Cyanobacteria, Cytophaga, Dialister, Enterobacter, Enterobacter cloacae, Enterobacter cowanii, Enterobacteriaceae, Enterobacteriales, Escherichia, Escherichia coli, Escherichia fergusonii, Fimbriimonas ginsengisoli, Fusobacterium necrophorum, Fusobacterium nucleatum, Fusobacterium polymorphum, Haemophilus haemolyticus, Haemophilus influenzae, Helicobacter, Helicobacter pylor, Klebsiella pneumoniae, Legionella, Legionella pneumophila, Leptotrichia buccalis, Escherichia coli, Luteimonas aestuarii, Luteimonas aquatica, Luteimonas composti, Luteimonas lutimaris, Luteimonas marina, Luteimonas mephitis, Luteimonas vadosa, Megamonas, Megasphaera, Meiothermus, Methylobacterium fujisawaense, Morax-Axenfeld diplobacilli, Moraxella, Moraxella bovis, Moraxella osloensis, Morganella morganii, Negativicutes, Neisseria cinerea, Neisseria gonorrhoeae, Neisseria meningitidis, Neisseria sicca, Nitrosomonas eutropha, Nitrosomonas halophila, Nitrosomonas oligotropha, Pectinatus, Pelosinus, Pontiac fever, Propionispora, Proteobacteria, Proteus mirabilis, Proteus penneri, Pseudomonas, Pseudomonas aeruginosa, Pseudomonas, Pseudomonas luteola, Pseudoxanthomonas broegbernensis, Pseudoxanthomonas japonensis, Rickettsia rickettsii, Salmonella, Salmonella bongori, Salmonella enterica, Salmonella enterica* subsp. *enterica, Selenomonadales, Serratia marcescens, Shigella, Sorangium cellulosum, Sphaerotilus, Spirochaeta, Spirochaetaceae, Sporomusa, Stenotrophomonas, Stenotrophomonas nitritireducens, Thermotoga neapolitana, Trimeric autotransporter adhesin, Vampirococcus, Verminephrobacter, Vibrio adaptatus, Vibrio azasii, Vibrio campbellii, Vibrio cholerae, Vitreoscilla, Wolbachia*, or *Zymophilus*.

The bacterial strain to be utilized ideally is an avirulent strain. The skilled artisan recognizes that any naturally virulent bacteria may be genetically engineered to be avirulent or otherwise rendered to be avirulent by any means, including loss of one or more virulence factors, such as loss of at least one virulence plasmid and/or bacteriophage. In some cases, a naturally occurring avirulent version of a normally virulent bacteria may be employed.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Embodiments

In particular embodiments, one can generate a variety of modified lipooligosaccharide (LOS), consisting of core regions of LPS and lipid A molecules created by heterologous expression from plasmids or the chromosome of single or combinations of acyltransferase, deacylases, phosphatase and/or glycosyltransferases enzymes or through mutation of global regulatory genes required for regulating lipid A biosynthesis in an attenuated (BSL2-safe) hypo-acylated *Y. pestis* background. This exemplary strain when grown at mammalian temperatures produces a bisphosphorylated tetra-acylated structure that does not elicit proinflammatory responses in a variety of in vitro and in vivo assays. Methods of the disclosure allow one to use enzymes obtained from a wide variety of bacterial backgrounds (Table 1). These enzymes have specificities for fatty acid chain length additions either on the diglucosamine backbone of lipid A or acyl-oxy-acyl on these primary fatty acids, the removal of specific fatty acids or phosphate residues from the diglucosamine backbone, or more global changes due to directed mutations in either the sensor kinase or response regulator of various two-component regulatory systems, for example. Individually modified, rationally-designed lipid A structures are characterized using a variety of mass spectrometry and gas chromatography-based methodologies (as examples) to confirm the overall structure of the lipid A in the disclosed strains to generate using BECC.

Modified LOS/Lipid A structures can be tested in both in vitro and in highly relevant in vivo animal model(s) as stand-alone immunotherapeutic molecules or adjuvants in new immunogenic (including vaccine) formulations. As compared to impure and low-output MPL or AGPs, respectively, engineered lipid A-based structures can be: (1) produced efficiently, (2) fully characterized using mass spectrometry and gas chromatography-based methodologies for structure and purity, and (3) produced rapidly in sufficient quantities for use in preclinical and clinical testing and for clinical use. Additionally, adjuvanticity with a subset of LOS/lipid A structures are confirmed using an engineered murine strain expressing human TLR4 (humanized TLR4; Hajjar et al., 2012) to more closely mimic human immune responses and address potential discordance in LPS recognition by human compared with mouse TLR4/MD-2 (Kawai and Akira, 2011; Pasare and Medzhitov, 2005). Ultimately, assessment of the adjuvant characteristics of BECC synthesized molecules via murine and human TLR4 results in an increased understanding of humoral and cell-mediated immunity to a variety of ligands that induce $T_H1$-$T_H17$- and $T_H2$-type immune responses in the systemic and mucosal compartments of the host, in at least some embodiments.

Once individual structures are verified, one can test the immunotherapeutic potential of these new molecules using standard, proven in vitro and in vivo assay to determine if any of these molecules represent adjuvants and/or immunomodulating reagents. One can also include a well-known available reference adjuvant, such as MPL as a head-to-head comparison to the molecules synthesize by BECC. Embodiments of the disclosure provide major implications in the field of antigen recognition, formulation, and vaccine design.

Example 2

Construction of Rationally-Designed Los/Lipid a Structures with Engineered Lipid a Modifications Using Bacterial Enzymatic Combinatorial Chemistry (BECC)

In one aspect of the disclosure, there is custom synthesis of LOS/lipid A molecules using heterologous expression of bacterial enzymes required for LPS biosynthesis (acyltransferases, glycosyltransferases, phosphatases, and/or kinases, for example), and through manipulation of global regulatory or biosynthesis genes in an attenuated Yp background (as an example of a background). A variety of mass spectrometry and gas chromatography-based methodologies can be used to verify that the correct lipid A modifications have been synthesized.

In initial analysis, there is synthesis of proof-of-concept adjuvant/immunotherapeutic LOSs with modified lipid A anchors. In specific embodiments, three BECC Yp strains that produce unique LOS/lipid A structures when grown at 37° C., mammalian host temperature (Table 1) are provided herein. BECC-generated LOS were tested in in vitro stimulation studies; the ΔphoP 37° C. tetra-acylated structure was compared directly to the approved adjuvant, MPL, in an in vivo, vaccination study described elsewhere herein.

Construction of additional rationally-designed LOS/lipid A structures with modified lipid A structures using BECC is achieved. One can create and validate safe-to-use, attenuated *Y. pestis* (Yp) strains with modified LOS/lipid A molecules that are subsequently screened for immunogenic potential in vitro and in vivo. Useful to the design of BECC are well-characterized enzymes sourced from a variety of bacterial species (FIG. 8 provides a list of cloned enzymes). Novel to BECC is the heterologous expression of these modifying enzymes in an attenuated Yp background, such as KIM6 or KIM10, to engineer unique lipid A structures. Bacterial conjugation, electroporation, or bacterial mating may be utilized to introduce genes from an enzyme library into the Yp KIM6 parent chromosome or via exchange of expression plasmids (Jones et al., 2010; Rebeil et al., 2004; Donenberg and Kaper, 1991). An example of a scheme of use for the individual modifying genes is based on known structure/function interaction of specific modifications and the host innate immune receptor (TLR4) and may be prioritized as follows: 1) mutations in global regulators of lipid A modifications, 2) altering the level of fatty acid content through the addition or deletion of acyltransferases and/or deacylases, 3) expression of phosphatase to specifically remove one of the terminal phosphates on the lipid A backbone, and 4) expression of glycosyltransferases that will add specific sugar residues to the terminal phosphate residues. Strains may be vetted by a combination of MALDI-TOF MS for initial lipid A structural confirmation followed by higher order MS (ESI) to provide intimate structural detail and molecular design validation. One can use gas chromatography (GC) to quantify the percentage of total fatty acids of each respective modified lipid A structure, providing further verification that the correct strains have been generated and that they are both productive and accurate.

TABLE 1

BECC MODIFIED STRAINS OF YP

| | Strains | Strain Description |
|---|---|---|
| 1. | Wild-type Yp KIM6 | WT KIM6 (exempt select agent strain of Yp; lacks pigmentation locus and pCD1 plasmid; CDC BSL-2 classification) |
| 2. | KIM6-pagP+ | KIM6 with a repaired pagP gene (adds C16 fatty acid to lipid A) |
| 3. | ΔphoP-KIM6 | KIM6 with a deleted phoP gene, which is a member of a 2 component sensor kinase signaling system (a transcriptional regulator) |
| 4. | ΔphoP -pagP+ | KIM6 with a deleted phoP gene which is a member of a 2 component sensor kinase signaling system (a transcriptional regulator) and a repaired pagP activating gene which adds C16 fatty acids to lipid A |

Modifications in these strains have been confirmed by MS and GC analysis (data not shown). Corresponding major lipid A structures are indicated in FIG. 1.

Analysis of LOS and lipid A isolated from BECC constructed strains is provided herein. For initial screening, one can use two small-scale LOS extraction protocols that require small overnight cultures (~5 mls). These methods include a phenol-based (Yi and Hackett, 2000; Westphal and Juan, 1965) and an ammonium hydroxide/isobutyric acid-based (El Hamidi et al., 2005) protocol, which are repeatable and robust extraction techniques, standard methods in the Ernst laboratory. After extraction, lipid A will be liberated from these LOS preparations using gentle hydrolysis, which preserves structural elements (e.g., phosphate groups and attached carbohydrate moieties) that are sensitive to harsh acid treatment (Caroff et al., 1988) One can use a variety of mass spectrometric-based techniques, such as MALDI-TOF and ESI routinely used in the art to characterize the base structure of the lipid A in both the negative and positive-ion mode (Ernst et al., 2006). Large-scale LOS preparations are extracted using a hot phenol/water extraction method (Ernst et al., 2007; Ernst et al., 2006; West et al., 1997; Hajjar et al., 2006). Subsequently, LOS are treated to ensure purity from contaminating nucleic acids and proteins (Fischer et al., 1983) and converted to lipid A by mild hydrolysis. LOS samples are extracted to remove contaminating phospholipids (Folch et al., 1957) and TLR2-agonist proteins (Hirschfeld et al., 2000) thus generating preparations suitable for structural analysis and proinflammatory studies discussed proposed below. LOS/lipid A fatty acid content is measured by gas chromatography (GC) after acid hydrolysis, methylation, and hexane extraction (Guo et al., 1997; Somerville et al., 1996). The resultant $MS^n$ and GC data is used to define the exact structure of individual molecules present in the isolated lipid A from the WT and BECC constructed strain.

Example 3

Define Immunomodulatory Profile of Engineered Los/Lipid a Using an In Vitro Screening Model In this embodiment, it is demonstrated that the rationally-designed, validated molecules generated by methods herein produce altered innate responses. One can characterize BECC synthesized molecules for innate immune responses mediated via TLR4 in a dose dependent manner to allow for the selection of candidate molecules for use in in vivo adjuvanticity-based assays. One can utilize murine macrophage cell lines (RAW and MH-S) and human cell lines (U937 and THP-1) along with primary macrophage cells from mice (PES) and humans (PBMCs obtained from Lonza as buffy coats) in cell stimulation studies using a wide dose range of LOS/lipid A. Both LOS and lipid A preparation are tested to rule out any role for the core region of LOS in altering innate immune responses. Preliminary cell stimulation screening of supernatants is performed using cytokine/chemokine ELISAs (Hajjar et al., 2006; Darveau et al., 1995; Guo et al., 1998; Grkovich et al., 2006). Stimulation of TLR4 and broad innate immune activation via the NF-κB and TRIF/TRAM arms of proinflammatory signaling pathways will be demonstrated by secretion of IL-8 and RANTES/IL-1β. TLR4 signaling through NF-κB (MyD88-dependent) results in secretion of the neutrophil recruiting chemokine IL-8, similarly TRIF/TRAM (MyD88-independent) will also promote lymphoattraction, but through the expression of RANTES (CCL5) driven by the transcription factor AP-1. These chemokines contribute to prompt, effective immune activation and help describe the mechanism-of-action for LOS-based adjuvant molecules. Deep profiling of cell stimulation by modified LOS/lipid A is performed using cytokine multiplex assays to illustrate activation of cell-mediated and/or humoral pathways (Coler et al., 2011; Man et al., 2010; West et al., 2008). To supplement the secreted protein profiling, RNA harvested from stimulated human cells is analyzed by qPCR for cytokine/chemokine gene expression (Meng et al., 2011; Coats et al., 2009). Selection of candidate molecules for use in the subsequent in vivo screening assays is based on combination and rank-ordering of the cytokine and gene expression profiles. Priority can be given to molecules that have low toxicity and remain immunostimulatory as defined by the cytokine profile (i.e.: triggering chemotaxis, but not profound apoptosis or pyroptosis). Particular modified LOS/lipid A molecules are forwarded into in vivo screening in at least some cases. This strategy delineates a rational triage schedule to screen potential immunotherapeutic candidates.

Figure 2:
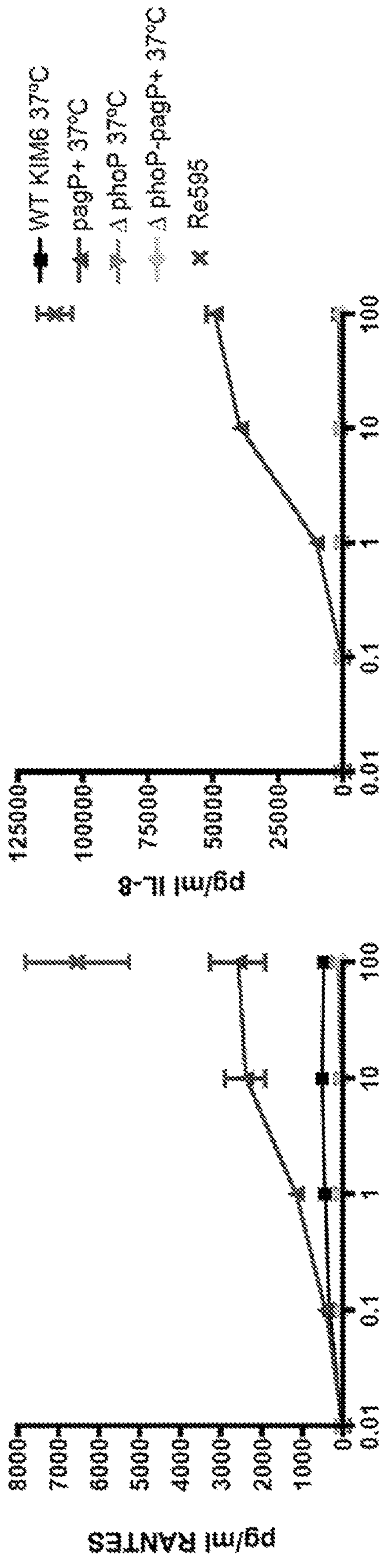
FIG. 2 demonstrates that a modified Yp LOS is immunostimulatory. Purified LOS was tested by an in vitro cell stimulation assay using differentiated (Vitamin $D_3$) THP-1 cells. Dose-response stimulations with LOS for 24 hours, supernatants were assayed by ELISA for IL-8 and human RANTES (R&D Sys.). Re595 response at 100 ng/mL, a potent TLR4 agonist positive control; +37 C, illustrates potency of rational modification of a non-stimulatory (WT) structure. GlaxoSmithKline (GSK) and Avanti MPL (slightly different lipid A structures), response at 1 μg/ml for RANTES is 641 pg/ml and 147 pg/ml, respectively. No response was observed at 100 μg/ml.

Highlighting the feasibility of using an in vitro screening model to progress candidate molecules to further in vivo work is illustrated in FIG. 2. FIG. 2 demonstrates that an engineered LOS with hexa-acylated lipid A from the KIM6 pagP expressing strain grown at mammalian host temperature induces secreted cytokines IL-8 and RANTES in contrast to the absence thereof by the WT base. The pagP enzyme is non-functional in all Yp strains. MPL (from major manufacturers) tested over the same dose-response manner only respond at the very highest doses. A 4-log dose increase was necessary to elicit a RANTES response approaching the engineered LOS at 0.1 ng/mL (pagP+37° C.). Furthermore, ~3-fold differences in response were observed between the two sources of MPL even at 1 μg/ml. Therefore, structural heterogeneity of MPL resultant from the nature of chemical synthesis (FIG. 1) alters its potency dramatically. These data illustrate engagement of both the MyD88-dependent and -independent arms of the TLR4 signaling pathway by modified LOS. Surprisingly, LOS from the pagP expressing, ΔphoP strain is a poor inducer of either cytokine readouts, suggesting an important role for this global regulator in controlling more global Yp lipid A modifications. GC analysis shows that the ΔphoP-pagP+ strain has ~50% less C16 fatty acid in its lipid A as compared to the pagP+ lipid A.

Example 4

Define Efficacy of Immunomodulatory Candidates as Adjuvants and/or Stand-Alone Agents Using In Vivo Murine Screening Models In one embodiment of the disclosure, the immunogenic potential of a candidate molecule to alter innate and adaptive responses in vivo is demonstrated. One can develop molecules that will have low cytoxicity yet retain the ability to activate the innate and adaptive immune responses in vivo and also confer protection against virulent bacterial strains in a murine vaccine model as highlighted elsewhere herein. Particular molecules generated herein that are potent immune stimulants without being overtly cytotoxic are administered to mice both alone and with known immunogenic reagents to probe innate and adaptive immune potentiation, specifically direct modulation of cell mediated and humoral immunity and balancing of $Th_1/Th_2$ response. Additionally, the use for LOS/lipid As as an immunoprophylactic to a lethal challenge of infectious agent is analyzed. In at least some cases, there are mice expressing murine TLR4 alone and with known immunogens to access toxicity and activation of the innate and adaptive immune responses in murine vaccine models (intranasal and intramuscular). Subsequently, LOS/lipid A structures with potential adjuvanticity are confirmed using an engineered murine strain expressing human TLR4 to more closely mimic human immune responses.

Figure 3:
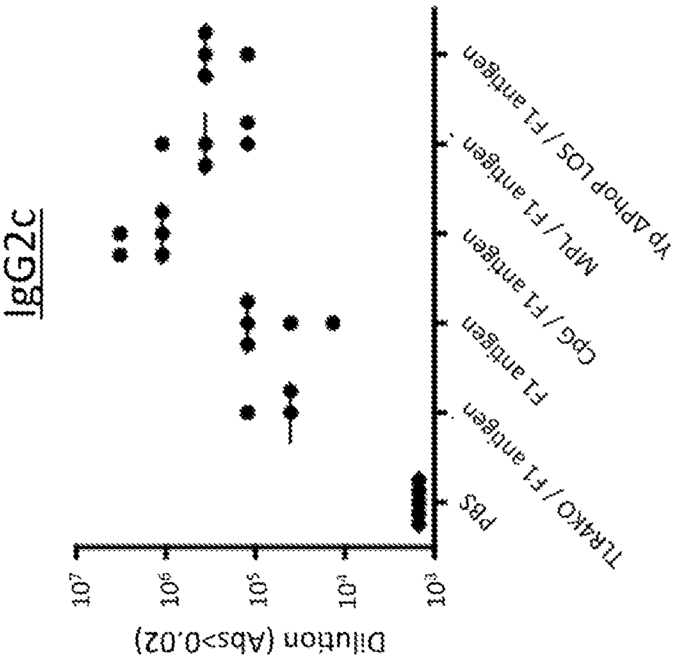
FIG. 3 shows that modified LOS enhances adaptive immune response to protein antigen. C57BL/6 mice were dosed, IP, with F1 protein antigen in combination with possible adjuvant candidate ΔphoP 37° C., boosted at 4 weeks, serum was harvested 1 week post-boos and IgG subtypes tittered by ELISA. Dosing regimen used; 25 μg Yp F1+/−50 μg CpG, Avanti MPL, and ΔphoP LOS.
Figure 4A:
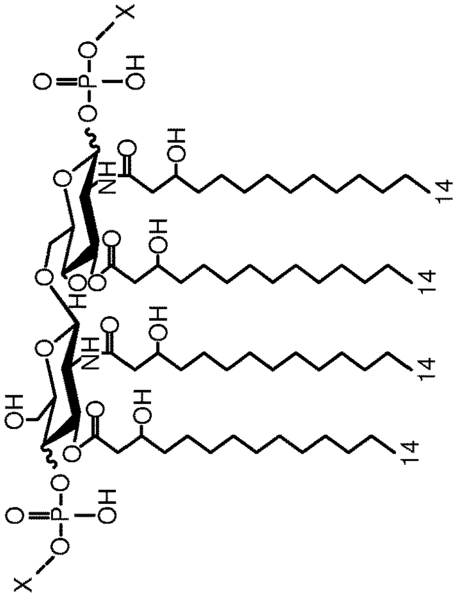
FIGS. 4A-4E illustrate representative Yp-based lipid A structures (FIGS. 4B-4C) generated using BECC, as compared to WT Yp grown at 37° C.
Figure 4B:
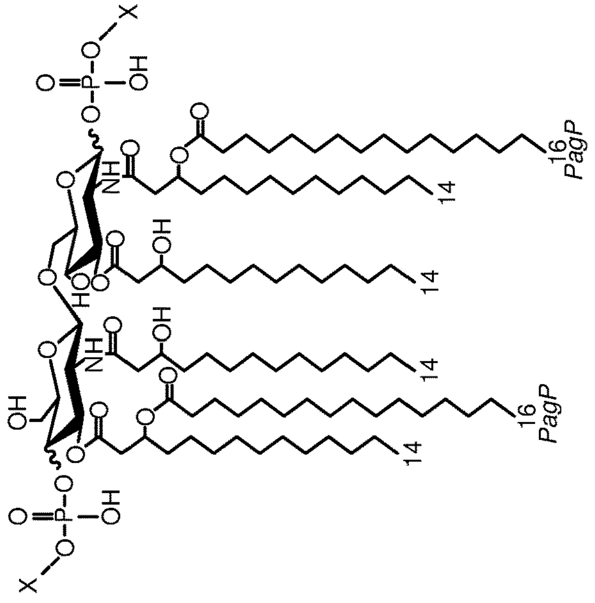
Figure 4C:
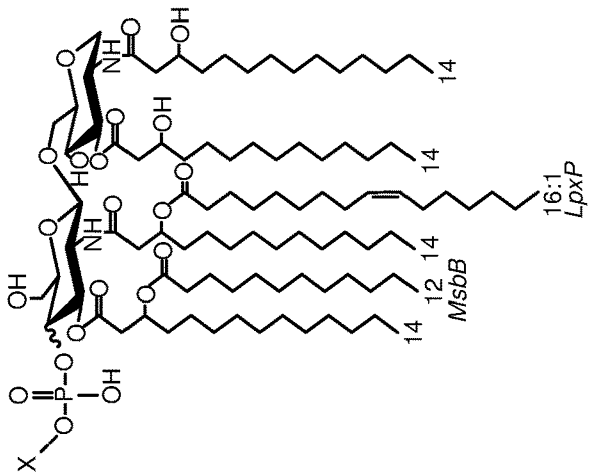
Figure 4D:
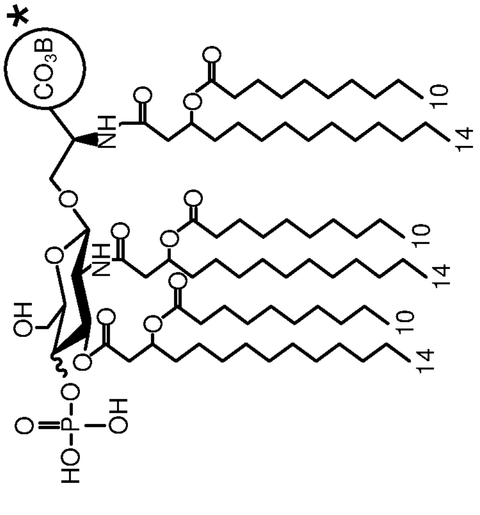
Figure 4E:
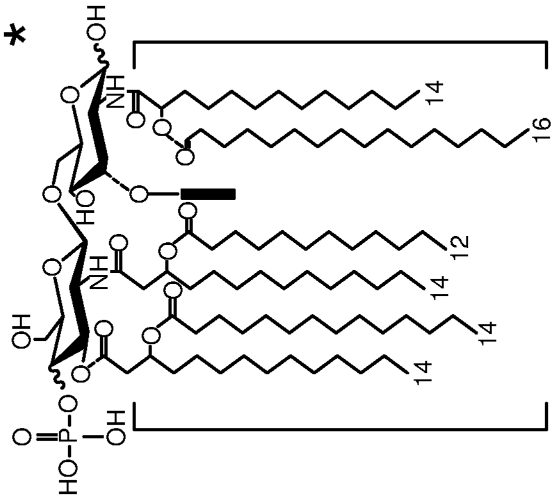

Modified LOS from strains in the WT Yp background can induce an adaptive immune response when used with other known immunogenic reagents in in vivo murine vaccine experiments. The ability to design and use Gram-negative bacterial strains containing alterations in lipid A structure that confer protection in in vivo murine disease models (Hajjar et al., 2006; Lai et al., 2010; Kanistanon et al., 2008; West et al., 2008; Lembo et al., 2008) is known, and validation of this strategy is shown in FIG. 3. These data show proof-of-principle that modified LOS used as an adjuvant in combination with Yp capsular F1 Ag evokes an adaptive immune response equal to the approved adjuvant MPL; inducing a IgG2c antibody response, indicative of a $Th_1$ response, as well as a $Th_2$-driven IgG1 response equal to MPL and ODN2395 (CpG) in a murine mouse model. This mode of adaptive immune activation is TLR4-dependent as it is not observed in TLR4-KO mice and is suggestive of a balanced $Th_1/Th_2$ profile that is an asset for optimization of immunogenic composition design, including vaccine design.

One can define cytotoxicity of engineered molecules using in vivo murine screening models. To determine the toxicity in each biologically-relevant candidate, escalating doses (0.5 μg, 5 μg, 50 μg, with mock controls) are delivered by intraperitoneally (IP) injection to C57BL/6 (The Jackson Laboratory), 5 mice/dose group. Mice are followed for survival and signs of acute toxicity. Necropsies are performed at study-end to survey signs of damage and/or toxicity by gross pathology or histology (as required). Compounds with absent or acceptably low toxicity are carried forward for further characterization.

One can demonstrate direct activation of the innate immune system by engineered LOS. To test the ability of modified LOS to stimulate the innate immune system in vivo, candidate escalating doses (0.5 μg, 5 μg, 50 μg with antigen only, MPL, and mock controls, as examples), are injected by the IV route into C57/BL6 mice. Sera are collected 2 hours post-injection for analysis. Cytokine profiles are determined by multiplex assays or ELISA and analyzed for specific early activation markers (ex: TNF-α, IL-1β, III III.).

An immunization strategy using LOS to potentiate adaptive immune responses in vivo is included in the disclosure.

To demonstrate that candidate molecules will activate adaptive immune responses in an in vivo murine model, C57/BL6 mice are randomly divided into groups, each consisting of five mice. Animals are dosed intraperitoneally (IP) with 25 μg of Yp F1 antigen alone and with 50 μg of candidate LOS, or MPL/ODN2395 (CpG) as controls (with necessary mock controls). 50 μg of the candidate LOS are also administered alone to test for stand-alone immunotherapeutic efficacy. Boosting injection is given 4 weeks later. Sera is collected 1 week after the second immunization to quantitate F1 antigen-specific antibodies (total IgG initially, class and subtype as relevant) by ELISA; concentrations of serum cytokines, hallmarks of immune activation (IL-2, IL-4, IFN-γ, TNF-α, IL-12, IL-8, etc.), will also be profiled by cytokine multiplex assays.

One can characterize protective immune responses to virulent *Y. pestis* conferred by LOS-based vaccine. Mice previously vaccinated (above) with candidate LOS adjuvant formulations will be used to test the durability of the induced adaptive immune responses from a lethal challenge using the fully virulent CO92 strain of Yp. Two weeks after the second boost dose (study week 6), mice will be challenged with ~100×$LD_{50}$ (200-300 cfu) of CO92 by IP injection. Mice will be monitored for survival and signs of disease for 4 weeks.

In specific embodiments, any antigen is employed with one or more compositions of the disclosure.

Example 5

Generation of Rationally-Designed Adjuvants have Major Implications in the Field of Antigen and Adjuvant Formulation, and Vaccine Design Synthesis of adjuvant/immunotherapeutic LOS with modified lipid A structures is performed. BECC *Yersinia pestis* (Yp) strains are generated that produce unique lipooligosaccharide (LOS)/lipid A structures when grown at host (37° C.) or environmental (26° C.) temperatures. Plasmids expressing individual lipid A modifying enzymes were expressed in trans in the genetically tractable, avirulent Yp strains KIM6 or KIM10. Both strain backgrounds are exempt from select agents status and are approved for use under BSL-2 laboratory practices as they lack the pigmentation locus (pgm) and the pCD1 plasmid required for virulence (http://www.selectagents.gov). Examples of two of the BECC designed molecules, as compared to the structure of an AGP and MPL, are shown in FIGS. 4A-4E. To date, these BECC-generated LOS have been tested in initial in vitro stimulation studies; the ΔphoP 37° C. tetra-acylated structure has performed similarly to the approved adjuvant, MPL in an in vivo, proof-of-concept vaccination study below.

Figure 5:
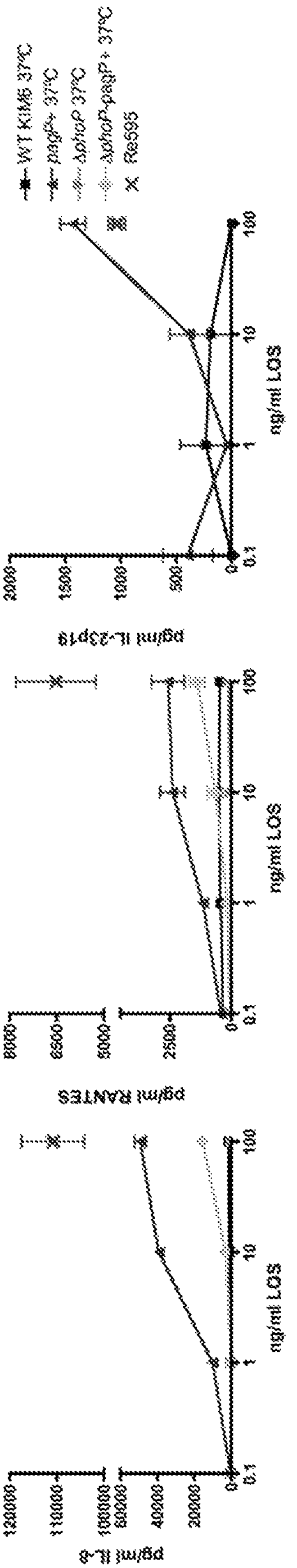
FIG. 5 shows that modified Yp LOS is immunostimulatory. Purified LOS was tested by an in vitro cell stimulation assay using differentiated (Vitamin D3) THP-1 cells. Dose-response stimulations with LOS for 24 hours, supernatants were assayed by ELISA for IL-8, human RANTES, and IL-23. Re595, a potent TLR4 agonist was used as a positive control at 100 ng/mL; pagP+37° C. LOS illustrates potency of rational modification of a non-stimulatory (WT) structure. MPL obtained from GSK and Avanti (slightly different lipid A structures) response at 1 mg/ml for RANTES is 641 pg/ml and 147 pg/ml, respectively. No response was observed at 100 μg/ml.
Figure 7:
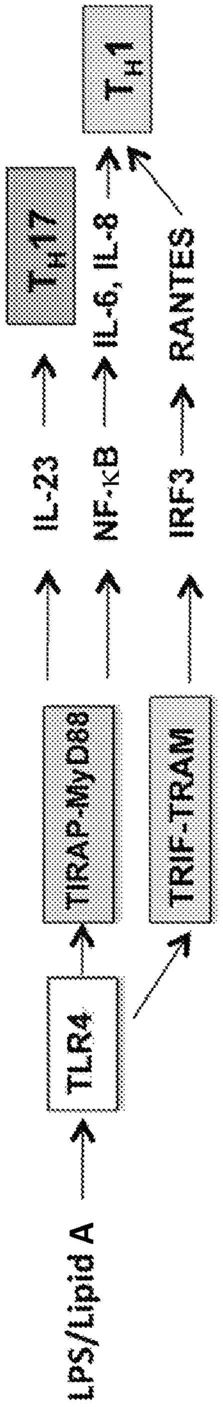
FIG. 7 shows examples of pathways of adjuvant outcomes for TLR4 activation.
Figure 20:
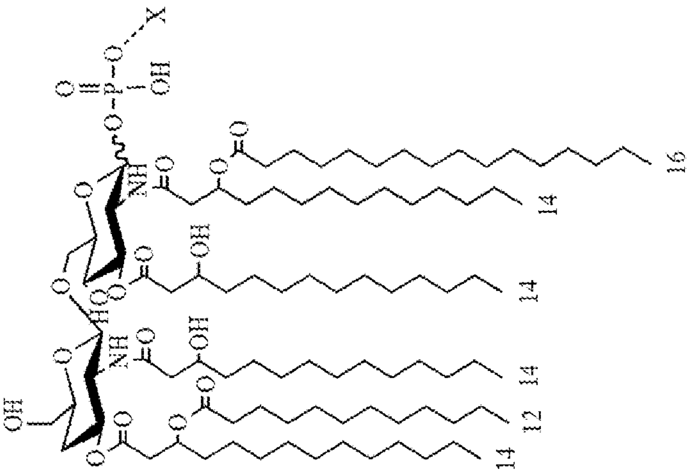
FIG. 20 demonstrates the structure of an exemplary LPS molecule generated by methods of the disclosure.

BECC-synthesized LOS molecules have altered innate immune responses. Highlighting the feasibility of using an in vitro screening model to progress candidate molecules to further in vivo work is illustrated in FIG. 5. FIG. 5 demonstrates that an engineered LOS with hexa-acylated lipid A from the KIM6 pagP expressing strain grown at mammalian host temperature stimulated secretion of cytokines IL-8, RANTES, and IL-23 from THP-1 cells. MPL (GSK and Avanti) tested over the same dose-response manner only respond at the very highest doses. A 4-log dose increase was necessary to elicit a RANTES response approaching the engineered LOS at 0.1 ng/mL (pagP+37° C.). Furthermore, ~3-fold differences in response were observed between the two sources of MPL even at 1 μg/ml. Therefore, MPL potency suffers dramatically from structural heterogeneity, a result of the nature of chemical synthesis (FIGS. 4A-4E). These data illustrate that modified LOS engages both the MyD88-dependent and -independent arms of the TLR4 signaling pathway (FIG. 7). Surprisingly, LOS from the pagP expressing, ΔphoP strain is a poor inducer of either cytokine readouts, suggesting an important role for this global regulator in controlling more global Yp lipid A modifications. GC analysis shows that the ΔphoP-pagP+ strain has ~50% less C16 fatty acid in its lipid A, as compared to the pagP+ lipid A.

Figure 6:
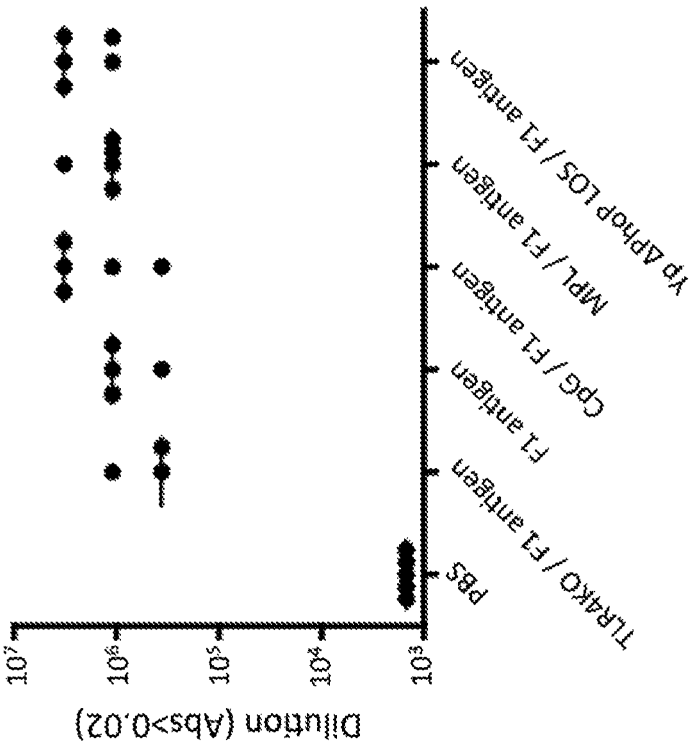
FIG. 6. Provides that modified LOS enhances adaptive immune response to protein antigen. C57BL/6 mice were dosed, IP with F1 protein antigen in combination with possible adjuvant candidate ΔphoP 37° C., boosted at 4 weeks, serum was harvested 1 week post-boost and IgG1 titered by ELISA. Dosing regimen used: 25 μg Yp F1 antigen; 50 μg CpG, MPL, or Yp ΔphoP LOS.

Modified LOS enhances adaptive immune response to protein antigen. It is demonstrated that modified LOS from strains in the WT Yp background can induce an adaptive immune response when used with other known immunogenic reagents in in vivo murine vaccine experiments. Validation of this strategy is shown in FIG. 6. These data show that BECC-synthesized Yp LOS can be used as an adjuvant in combination with Yp capsular F1-V Ag and evokes an adaptive immune response equal to the approved adjuvant MPL and ODN2395 (CpG) in a murine mouse model. This mode of adaptive immune activation is TLR4-dependent as it is not observed in TLR4-KO mice and indicates that BECC-synthesized adjuvants are an asset for optimization of vaccine design.

Example 6

Construction of Rationally-Designed Los/Lipid a Structures with Engineered Lipid a Modifications Using Bacterial Enzymatic Combinatorial Chemistry (BECC)

An area of great interest is in the development of rationally-designed adjuvants based on molecules that stimulate the host innate immune system, specifically pattern-recognition receptors, including toll-like receptors (TLR). The objective of this aim is to custom synthesize LOS/lipid A molecules using heterologous expression of acyltransferases, glycosyltransferases, phosphatases, kinases, and modification of global regulatory genes required for lipid A biosynthesis with altered host innate immune responses.

Construction of additional rationally-designed LOS/lipid A structures with modified lipid A structures using bacterial enzymatic combinatorial chemistry (BECC) is encompassed in the disclosure. One can engineer modified LOS/lipid A molecules in an Yp background for determination of adjuvant potential using in vitro and in vivo assay systems. Briefly, one can heterologously express lipid A modifying enzymes in trans through bacterial conjugation or electroporation in a safe, attenuated BSL-2 Yp background (KIM6 or KIM10) to engineer unique lipid A structures (Donnenberg and Kaper, 1991; Rebeil et al., 2004; Jones et al., 2010) These Yp strain backgrounds were chosen as they produce a bisphosphorylated tetra-acylated lipid A structure (also known as lipidIVA) when grown at 37° C., thus allowing easy analysis of any resulting modification(s). As shown above, specific enzymes (PagP and MsbB) have been expressed in these Yp strain backgrounds to generate unique proof-of-concept lipid A structures. In addition, there are engineered strains that lack the two-component transcriptional regulator (PhoP) required for global lipid A modifications. These lipid A molecules are currently being evaluated for altered innate immune responses and adjuvant potential. These molecules are capable of inducing immune responses that can lead to either TH1 and/or TH17 responses. T helper responses are essential to the development of high affinity and long-term protective immunity. The specific T helper response can alter antibody isotype that can effect affinity, and avidity, as well as interactions with other immune cells required for pathogen clearance. To date, all previously reported BECC-derived molecules are bisphosphorylated (phosphate moieties at the 1 and 4' position). As has been shown for the AGP and MPL molecules, the presence of the phosphate moiety at the 1 position on the glucosamine backbone of lipid A plays an important role in host innate immune recognition. Therefore, one can focus on expressing enzymes that remove the terminal phosphate moieties in the strains that already have been generated by BECC. Two phosphatases have been identified in *Francisella novicida* that remove the 1 position (LpxE) and 4' position (LpxF) phosphatases (Wang et al., 2004; Wang et al., 2007) One can generate six additional bacterial mutants that express acyltransferases (LpxP, HtrB, LpxXL) and glycosyltransferases (addition of aminoarabinose and galactosamine) or deletions in other global regulators (PmrA/B) using plasmid constructs currently available in an enzyme expression library (Raetz et al., 2007).

Aspects of the disclosure provide analytical validation of LOS and lipid A isolated from BECC constructed strains. For initial screening, one can use two small-scale LOS extraction protocols that require small overnight cultures (~5 mls). These methods include a phenol-based (Yi and Hackett, 2000; Westphal and Juan, 1965) and an ammonium hydroxide/isobutyric acid-based (El Hamidi et al., 2005) protocol, which are repeatable and robust extraction techniques and standard methods in the Ernst laboratory. After extraction, lipid A is liberated from these LOS preparations using gentle hydrolysis, which preserves structural elements (e.g., phosphate groups and attached carbohydrate moieties) that are sensitive to harsh acid treatment (Caroff et al., 1988). One can use a variety of established mass spectrometric-based techniques, such as MALDI-TOF and ESI, to characterize the base structure of the lipid A in both the negative- and positiveion mode (Ernst et al., 2006). Large-scale LOS preparations are extracted using a hot phenol/water extraction method (Hajjar et al., 2006; Ernst et al., 2006; West et al., 1997; Ernst et al., 2007).

Subsequently, LOS are treated to ensure purity from contaminating nucleic acids and proteins (Fischer et al., 1983), extracted to remove contaminating phospholipids (Folch et al., 1957) and TLR2-agonist proteins (Hirschfeld et al., 2000), and when required, converted to lipid A by mild hydrolysis. These steps ensure the generation of preparations suitable for structural analysis and proinflammatory and adjuvanticity experiments proposed below. LOS/lipid A fatty acid content are measured by gas chromatography (GC) after acid hydrolysis, methylation, and hexane extraction (Guo et al., 1997; Somerville et al., 1996). The resultant MS and GC data is used to define the exact structure of individual molecules present in the isolated lipid A from the WT and BECC constructed strain.

Example 7

Immune Responses to Novel Los/Lipid a Molecules

BECC-synthesized molecules produce innate immune responses mediated via TLR4 in a dose-dependent manner, similar to AGP and MPL and the resulting analysis of host immune responses allow for the selection of candidate molecules for use in in vivo adjuvanticity studies.

Current lipid A mimetics, such as AGP and MPL differentially activate the NF-KB and TRIF/TRAM signaling pathways, as compared to LPS leading to altered secretion profiles of proinflammatory cytokines and chemokines. One can demonstrate that the rationally-designed, validated molecules produce altered innate responses. Initially, one can utilize HEK293 cells transfected with TLR4 to determine host innate immune responses to our BECC synthesized molecules (Rebeil et al., 2004; MacArthur et al., 2011; Hajjar et al., 2006; Miller et al., 2005). Subsequently, as many adjuvants induce the innate immune response by promoting dendritic cell (DC) cell maturation resulting in the priming of naive T cells and initiating potent immune responses, one can test LOS/lipid A preparations in murine and human DCs (Arias et al., 2012; Seregin et al., 2011). Both LOS and lipid A preparations are tested to rule out any role for the core region of LOS in altering innate immune responses.

TLR4 restriction/dependence of novel engineered LOS/lipid A molecules is demonstrated. To determine the restriction of the molecules to TLR4, HEK293 cells are utilized. HEK293 cells are transfected with murine or human MD2/TLR4 and incubated with increasing concentrations (0.01 ng/ml. 0.1 ng, ml, 1 ng/ml, 10 ng/ml, 100 ng/ml) of novel LOS and lipid A preparations for 4 and 24 hours. Supernatant is harvested and analyzed for cytokine production (TNF-α, IL-6, IL-12 p40, IL-23 p19, RANTES) by ELISA. Analysis of these cytokines can confirm that the BECC synthesized molecules are only active when MD-2/TLR4 is expressed and determine whether the molecules are signaling through MyD88-TIRAP, TRIF-TRAM, or a combination of both. As can be seen in FIG. 7, the TLR4 signaling adapter can influence the T helper cell response to either a TH1 alone or a combination of TH1 and TH17. T helper subtype have a marked effect on the subtype of antibody produced, which in turn can help or hinder the effectiveness of the antibody response. Finally, to determine cellular cytotoxicity, the release of LDH in the supernatant will be measured by colorimetric assay.

There is maturation of Dendritic Cells upon novel adjuvant treatment. Dendritic cells (DCs), the quintessential antigen presenting cells (APC), have the ability to interact with many immune partners simultaneously. To determine if DCs are activated by the BECC-synthesized molecules, one can stimulate both bone marrow derived DCs from mice, as well as peripheral blood DCs isolated from human donors as described above. Supernatants are harvested and analyzed for cytokine production (the interferon-γ induced chemoattractants CXCL10 and CXCL11, the T cell growth factor IL-2, the inflammatory mediators RANTES, and IL-6, as well as the growth factor GM-CSF) by ELISA or multiplex cytokine arrays. In addition to secreted cytokines level analysis, cells are harvested and their maturation is quantified by multicolor flow cytometry for the co-stimulatory molecules CD80 (B7-1) and CD86 (B7-2), as well as CD40 and MHC-class II. Increased surface expression of these molecules is a marker for the ability of DCs to present antigen and stimulate adaptive immune cells (Seregin et al., 2011; Coler et al., 2011).

Priority can be given to molecules that have, in the following order: (1) low toxicity, (2) remain immunostimulatory as defined by the cytokine profile (i.e., minimal NFKB activity; elevated TRW/TRAM and TH17 activity) and/or (3) have shown positive adjuvanticity potential in preliminary experiments (Yp ΔphoP mutant).

Example 8

Determine Immune Responses for Adjuvant Candidates Using In Vivo Murine Screening Models In particular embodiments, a low cellular cytotoxicity TLR4 mimetic has the ability to active the innate and adaptive immune responses in vivo and to confer protection against lethal bacterial infection in murine vaccine models. Two particular molecules (a $T_H1$ and $T_H1/T_H17$ modulator) identified by methods of the disclosure as being discriminating immune stimulants without overt cytotoxic effects are administered to mice both alone and with known immunogenic reagents to probe innate and adaptive immune potentiation, specifically the direct modulation of either a strict $T_H1$ or a mixed immune response $T_H1/T_H17$.

There is determination of cytotoxicity of and cytokine response to BECC-synthesized molecules using in vivo murine models. To determine the potential toxicity of each candidate molecule, serum sampling, as well as organ histology is carried out as described in Scheme 1. Serum samples are collected from all mice prior to any manipulation to measure baseline enzyme and cytokine levels. Two week after this initial serum harvest, escalating doses of BECC synthesized LOS or lipid A (0.5 μg, 5 μg, 50 μg, with mock control) are delivered by the intranasal (IN) route to C57BL/6 mice (n=3, The Jackson Laboratory). In an exemplary scheme (Scheme 1) for inoculation and sampling schedule to determine LOS/lipid A toxicity, on Day 0 a baseline serum is obtained, followed by adjuvant dose #1 at Day 14, serum harvest at day 28, adjuvant does #2 and serum harvest at day 42, serum harvest at day 56, and organ and serum harvest at day 60.

Both LOS and lipid A preparation are tested to determine if the core region of LOS plays a role in potential adjuvant responses. The IM route models the classical route of vaccine injection, while the IN route should induce mucosal-targeted immune responses. Mice are followed daily for survival and signs of acute toxicity. Every two weeks, peripheral blood is drawn for serum analysis. Analysis for toxicity in serum includes measurements for kidney (creatinine, BUN) and liver (ALT, AST, INR and total protein) damage by either ELISA or enzymatic assay. At one month after the initial dosing, mice receive a second dose of adjuvant and followed for an additional month. Necropsies are performed at study-end to survey signs of damage and/or toxicity by gross pathology or histology. Serum samples are also profiled by cytokine multiplex assays for the production immune activation (IL-2, IL-4, IFN-γ, TNF-α, IL-12 p40 or p70, IL-8). BECC synthesized molecules that have little to no toxicity, as well as robust cytokine profiles are carried forward for further characterization.

Evaluation of antigen-specific responses driven by engineered adjuvants is performed. To evaluate the ability of the BECC-synthesized molecules to generate antigen specific responses, two different bacterial antigens are assayed, F1-V capsular antigen (F1-V) from *Yersinia pestis*, as well as Pertussis Toxin (PT) from *Bordetella pertussis*. The F1-V antigen has been shown to be immunogenic and impart a protective immune response when combined with a known adjuvant (Heath et al., 1998; Jones et al., 2006). The PT antigen was chosen to demonstrate the ability of the helper cell polarization, a measure of maturation of the immune response (Ma et al., 2012). Each antigen is used at a concentration of 10 μg, as determined from published studies and administered with BECC synthesized molecules at the same doses used above. Control mice receive antigen coupled with CpG (ODN2095) or antigen with MPL as a positive control (Alving et al., 2012). Overall immune activation is tested by cytokine multiplex assay on harvested serum as defined in Scheme 2.

In scheme 2 for inoculation and sampling schedule to determine LOS/lipidA adjuvanticity, a baseline serum was obtained at day 0, adjuvant and antigen dose #1 were given at day 14, serum harvest occurred at day 28, adjuvant and antigen dose #2 and serum harvest occurred at day 42, serum harvest at day 56, and organ and serum harvest at day 60 (Lung BAL for IgG and IgA Titers and spleen for T cell responses). To determine if the molecules produce antigen-specific immunoglobulin(s), serum is analyzed for antigen-specific IgG and IgA by ELISA. In addition to total IgG and IgA, one can further explore the subclasses of IgG antibodies ($IgG_1$, $IgG_{2A}$, $IgG_{2B}$, $IgG_{2C}$, and $IgG_3$. These subclasses are influenced by the T helper response, a diversified repertoire of subclasses is indicative of a robust and varied T helper response. Lung localized antibodies are also analyzed in lavage fluids from mice at day 60. To determine the extent of T cell activation, spleens and lungs are harvested at day 60 and single cell suspensions are generated. These preparations are then re-stimulated with the administered antigen or the phorbol ester PMA and the ionophore ionomycin as a positive control. These cells are then analyzed by multicolor flow cytometry for TH1 (IFN-γ, IL-12, TNF-α), TH2 (IL-4, IL-5, IL-13), and TH17 (IL-17, IL-23) recall.

There is assaying of the protective capacity of F1-V antigen coupled with BECC synthesized molecules. Recent work has shown that coupling F1-V antigen with adjuvants (aluminum hydroxide, the proteasome based Protillin, and Complete Freund's Adjuvant (CFA)) can induce protective immune responses against a lethal wild type challenge (Heath et al., 1998; Jones et al., 2006; Parent et al., 2005a; Parent et al., 2005b). One can repeat and refine these studies using the novel adjuvants as follows: C57BL/6 mice are immunized with 10 μg F1-V antigen and our novel adjuvant as carried out above (Scheme 2). On day 60, mice are challenged with increasing doses of WT CO92 *Yersinia* (100 $LD_{100}$, 1,000 $LD_{100}$, 10,000 $LD_{100}$) by the IN route. Mice are followed for disease progression and survival for up to 120 days. To confirm the establishment of long-term protective immunity, adjuvant and antigen combinations that are protective at 60 days are used in a secondary study where mice are held for 120 days after this last vaccination before challenge.

There is assaying of the protective capacity of F1-V antigen coupled with BECC synthesized molecules by the intramuscular route. To determine if the adjuvants can deliver protection when administered by other routes one can test vaccination by the intramuscular (IM) route (Jones et al., 2006). huMD2/TLR4 mice are immunized with 10 μg F1-V antigen and the novel adjuvant by the IM route, as carried out above (Scheme 2). On day 60, mice are challenged with increasing doses of WT CO92 *Yersinia* (100 $LD_{100}$, 1,000 $LD_{100}$, 10,000 $LD_{100}$) by the IN route. Mice are followed for disease progression and survival for up to 120 days.

Confirmatory studies using humanized huMD2-TLR4 mice are performed MD2/TLR4 complexes from human and mouse have differing reactions to hypoacylated lipid A structures (i.e., murine TLR4 responds to all lipid A structures whereas human TLR4 differentially responds to specific lipid A structures) (Hajjar et al., 2012; Hajjar et al., 2002). To confirm that the BECC-synthesized adjuvants can provide protective immune responses when signaling through human MD2/TLR4 complexes, recently developed mice expressing huMD2/TLR4 are used in vaccination studies as carried out above in Scheme 2. Briefly, huMD2/TLR4 mice are vaccinated with two doses of 10 μg F1-V antigen along with the novel adjuvant. As a control, mice receive F1-V antigen along with CFA. Serum from these mice are analyzed for cytokine production (IL-2, IL-4, IFN-γ, TNF-α, IL-12, IL-8) by multiplex cytokine array. These mice are then challenged with increasing doses of WT CO92 *Yersinia* (100 LD100, 1,000 LD100, 10,000 LD100) on day 60 of the experiment. Mice are followed for disease progression and survival for up to 120 days.

Exemplary Methods with Vertebrate Animals

Female WT C57BL/6 mice (Jackson Laboratories) and huMD2/TLR4 mice (Breeding in house) are used.

Dendritic cell activation studies: Donor mice are harvested for bone marrow derived dendritic cells. 4 doses of adjuvant (0.5 μg, 5 μg, 50 μg and PBS control)×4 adjuvants (lipid A and LOS from 2 candidate molecules)×4 mice per experimental group=32 mice. These experiments are done in triplicate raising the total number of mice to 96.

Adjuvant toxicity studies: 3 doses of adjuvant (0.5 μg, 5 μg, 50 μg)×4 adjuvants (lipid A and LOS from 2 candidate molecules)×3 mice per group=36 mice+3 PBS dosed control mice=39 mice. These experiments will be done in triplicate raising the total number of mice to 117.

Antigen specific immune activation studies: 2 antigens (F1-V and PT)×3 doses of adjuvant (0.5 μg, 5 μg, 50 μg)×4 adjuvants (lipid A and LOS from 2 candidate molecules)×3 mice per group=72 mice+3 PBS dosed+3 CpG dosed control mice+6 CpG and Antigen dosed control mice (3 mice×2 antigens) 3 MPL dosed control mice+6 MPL and Antigen dosed control mice (3 mice×2 antigens)=93 mice. These experiments are done in triplicate raising the total number of mice to 289.

Adaptive immune activation and protection studies: Mice are divided into 2 test groups (adjuvant alone, adjuvant with F1-V antigen)×4 adjuvants (lipid A and LOS from 2 candidate molecules)×3 mice per group=24 mice. There are 4 control groups for the protection studies (PBS, F1 antigen alone, MPL with F1 antigen, CpG adjuvant with F1 antigen)×3 mice per group=12 mice, bringing the total to 36 mice. Mice are challenged by the IN route with 3 escalating doses of fully virulent CO92 strain of *Y. pestis* (36×3)=108 mice. If these mice demonstrate protection, this study will also be done in triplicate bringing the number of mice for this experiment to 324.

Long term protection studies: Mice are divided into 2 test groups (adjuvant alone, adjuvant with F1-V antigen)×4 adjuvants (lipid A and LOS from 2 candidate molecules)×3 mice per group=24 mice. There is one control group for the protection studies (PBS)=3 mice bringing the total to 27 mice. Mice are challenged by the IN route with 3 escalating doses of fully virulent CO92 strain of *Y. pestis* (27×3)=81 mice. If these mice demonstrate protection, this study will also be done in triplicate bringing the number of mice for this experiment to 243.

Confirmatory studies in huMD2/TLR4 mice: huMD2/TLR4 mice are utilized to rule out differential reactions between mouse and human TLR4. Mice are divided into 2 test groups (adjuvant alone, adjuvant with F1-V antigen)×4 adjuvants (lipid A and LOS from 2 candidate molecules)×3 mice per group=24 mice. There are 4 control groups for the protection studies (PBS, F1 antigen alone, MPL with F1 antigen, CpG adjuvant with F1 antigen)×3 mice per group=12 mice, bringing the total to 36 mice. Mice are challenged by the IN route with 3 escalating doses of fully virulent CO92 strain of *Y. pestis* (36×3)=108 mice. If these mice demonstrate protection, this study can be done in triplicate bringing the number of mice for this experiment to 324.

Protection through IM route vaccine delivery: To determine if IM vaccination of mice can still protect against an IN challenge huMD2/TLR4 mice are utilized for a final confirmatory study. Mice are divided into 2 test groups (adjuvant alone, adjuvant with F1-V antigen)×4 adjuvants (lipid A and LOS from 2 candidate molecules)×3 mice per group=24 mice. There are 4 control groups for the protection studies (PBS, F1 antigen alone, MPL with F1 antigen, CpG adjuvant with F1 antigen)×3mice per group=12 mice, bringing the total to 36 mice. Mice are challenged by the IN route with 3 escalating doses of fully virulent CO92 strain of *Y. pestis* (36×3)=108 mice. If these mice demonstrate protection, this study will also be done in triplicate bringing the number of mice for this experiment to 324.

Use of the Animals a. Dendritic Cell Activation:

Donor C57BL/6 mice are used for collection of BMDC. Femurs are harvested by sterile necropsy and marrow is flushed for in vitro differentiation.

b. Cytotoxicity Studies:

Initially, one can use C57BL/6 mice to determine the cytotoxicity of the adjuvant candidates. Five mice per treatment group are exposed by the intraperitoneal route to increasing doses (0.5 μg, 5 μg, 50 μg) of 1 of the 4 adjuvants identified to have the best immunomodulatory potential in the in vitro testing. All adjuvants are administered in 0.2 ml of PBS as a vehicle. Mice are visually checked twice daily for signs of distress or cytotoxicity. Every 14 days peripheral blood is harvested via the retro-orbital route for serum immune cytokines and toxicity panels (ALT, AST, etc). At the end of the test period (60 days), mice are necropsied to collect tissues for microscopic examination of any possible cytotoxic damage. This analysis is carried out in triplicate.

c. Antigen Specific Immune Activation Studies:

C57BL/6 mice are again used to test the ability of the adjuvant candidates to stimulate antigen specific immune response. Three mice per treatment group receive proven non-cytotoxic adjuvants, in the doses tested above, by the intramuscular and intranasal route. As controls 5 groups of mice are treated with one of; PBS, MPL, MPL+Antigen, CpG (ODN0295), or CpG+Antigen. Two hours after the injection serum is harvested from the mice and assayed by Luminex and RT-PCR for expression of pro-inflammatory cytokine and chemokines. This analysis is carried out in triplicate.

d. Adaptive Immune Activation and Protection Studies:

Adjuvants that have thus far been proven to be both safe and immunostimulatory are assayed for their ability to stimulate a protective immune response to a lethal pathogen. Groups of three mice are dosed with either 50 μg of adjuvant or adjuvant as well as 25 μg of purified *Y. pestis* F1-V antigen. Control groups will be dosed with PBS, 10 μg F1-V antigen alone, 50 μg MPL with 10 μg F1-V antigen, or 50 μg CpG (ODN0295) with 10 μg F1-V antigen. These mice receive a second "booster" dose 2 weeks after the initial dose. Mice are also assayed for their ability to survive a lethal challenge of 100, 1000, and 10000 $LD_{50's}$ ($LD_{50}$~5 cfu) of the fully virulent CO92 strain of *Y. pestis*. Four weeks after the boosting inoculation mice are challenged with *Y. pestis* by the subcutaneous route. Mice are visually checked twice daily for signs of disease (eye crusting, piloerection, inactivity, respiratory distress), mice showing disease symptoms are euthanized. If mice are able to survive the challenge the studies are repeated in triplicate.

Example 9

Exemplary Lipooligosaccharide/Lipid A-Based Mimetics

FIG. 9 provides a description of individual strains generated, structure of the resultant lipid A, and mass 37° C. Shown therein are examples of the *Y. pestis* KIM6 strains grown at 37° C. (mammalian temperature) with modified LOS structures. Accompanying major Lipid A structures can be examined in FIGS. 13-19 generally by referring to the capital letters in the Structure/Acylation column, e.g. use structure "C" to find the corresponding major lipid A structure on the following slides showing Lipid A structures.

FIG. 10 describes examples of the *Y. pestis* KIM6 strains grown at 26° C. (flea temperature) with modified LOS structures. Accompanying major Lipid A structures can examined in FIGS. 13-19 generally by referring to the capital letters in the Structure/Acylation column, e.g. use structure "C" to find the corresponding major lipid A structure in the following figures showing Lipid A structures.

FIG. 11 shows all results to date from cell stimulations using *Y. pestis* LOS grown at 37° C. (mammalian temperature) to stimulate the human THP-1 Vitamin D3 differentiated alveolar macrophage cell line. The headings above the secreted cytokines expressed show the pathway that is activated after innate immune recognition, e.g. IL-8 signaling is dependent on the MyD88 pathway. These data show that the modified LOS can induce cytokine production through 3 different pathways after initial recognition by the Toll-like receptor 4 (TLR4) complex. These data rankings are derived from a stimulus range of 0.1 to 100 ng/ml.

FIG. 12 shows results from cell stimulations using *Y. pestis* LOS grown at 26° C. (flea temperature) to stimulate the human THP-1 Vitamin D3-differentiated alveolar macrophage cell line. The headings above the secreted cytokines expressed show the pathway that is activated after innate immune recognition, e.g., IL-8 signaling is dependent on the MyD88 pathway. These data rankings are derived from a stimulus range of 0.1 to 100 ng/ml.

FIGS. 13-20 provide illustrations of exemplary LPS molecules generated by methods of the disclosure and referred to in FIGS. 9-10. FIG. 21 shows control LPS molecules.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PUBLICATIONS

Alving, C. R., et al., Adjuvants for human vaccines. Current Opinion in Immunology, 2012. 24(3): p. 310-5.

Arias, M. A., et al., *Glucopyranosyl Lipid Adjuvant* (*GLA*), *a Synthetic TLR*4 *agonist, promotes potent systemic and mucosal responses to intranasal immunization with HIVgp*140. PloS One, 2012. 7(7): p. e41144.

Bainbridge, B. W., et al., *Acyl chain specificity of the acyltransferases LpxA and LpxD and substrate availability contribute to lipid A fatty acid heterogeneity in Porphyromonas gingivalis*. Journal of Bacteriology, 2008. 190(13): p. 4549-58.

Berezow, A. B., et al., *The structurally similar, penta-acylated lipopolysaccharides of Porphyromonas gingivalis and Bacteroides elicit strikingly different innate immune responses*. Microbial Pathogenesis, 2009. 47(2): p. 68-77.

Caroff, M., A. Tacken, and L. Szabo, *Detergent-accelerated hydrolysis of bacterial endotoxins and determination of the anomeric configuration of the glycosyl phosphate present in the "isolated lipid A" fragment of the Bordetella pertussis endotoxin*. Carbohydrate Research, 1988. 175(2): p. 273-82.

Coats, S. R., et al., *Human Toll-like receptor* 4 *responses to P. gingivalis are regulated by lipid A* 1-*and* 4'-*phosphatase activities*. Cellular Microbiology, 2009. 11(11): p. 1587-99.

Coler, R. N., et al., *Development and characterization of synthetic glucopyranosyl lipid adjuvant system as a vaccine adjuvant*. PloS One, 2011. 6(1): p. e16333.

Darveau, R. P., et al., *The ability of bacteria associated with chronic inflammatory disease to stimulate E-selectin expression and neutrophil adhesion*. Progress in Clinical and Biological Research, 1995. 392: p. 69-78.

Donnenberg, M. S. and J. B. Kaper, *Construction of an eae deletion mutant of enteropathogenic Escherichia coli by using a positive-selection suicide vector*. Infection and Immunity, 1991. 59(12): p. 4310-7.

El Hamidi, A., et al., *Microextraction of bacterial lipid A: easy and rapid method for mass spectrometric characterization*. Journal of Lipid Research, 2005. 46(8): p. 1773-8.

Ernst, R. K., et al., *The Pseudomonas aeruginosa Lipid A Deacylase: Selection for Expression and Loss within the Cystic Fibrosis Airway*. Journal of Bacteriology, 2006. 188(1): p. 191-201.

Ernst, R. K., et al., *Specific lipopolysaccharide found in cystic fibrosis airway Pseudomonas aeruginosa*. Science, 1999. 286(5444): p. 1561-5.

Ernst, R. K., et al., *Unique lipid a modifications in Pseudomonas aeruginosa isolated from the airways of patients with cystic fibrosis*. The Journal of Infectious Diseases, 2007. 196(7): p. 1088-92.

Fischer, W., H. U. Koch, and R. Haas, *Improved preparation of lipoteichoic acids*. European Journal of Biochemistry/FEBS, 1983. 133(3): p. 523-30.

Folch, J., M. Lees, and G. H. Sloane Stanley, *A simple method for the isolation and purification of total lipides from animal tissues*. Journal of Bacteriology, 1957. 226 (1): p. 497-509.

Grkovich, A., C. A. Johnson, M. W. Buczynski, and E. A. Dennis, *Lipopolysaccharide-induced cyclooxygenase*-2 *expression in human U*937 *macrophages is phosphatidic acid phosphohydrolase*-1-*dependent*. J Biol Chem, 2006. 281(44): p. 32978-87.

Guo, L., et al., *Lipid A acylation and bacterial resistance against vertebrate antimicrobial peptides*. Cell, 1998. 95(2): p. 189-98.

Guo, L., et al., *Regulation of lipid a modifications by Salmonella typhimurium virulence genes phoP-phoQ*. Science, 1997. 276(5310): p. 250-253.

Hajjar, A. M., et al., *Human Toll-like receptor* 4 *recognizes host-specific LPS modifications*. Nature Immunology, 2002. 3(4): p. 354-9.

Hajjar, A. M., et al., *Humanized TLR4/MD-*2 *Mice Reveal LPS Recognition Differentially Impacts Susceptibility to Yersinia pestis and Salmonella enterica*. PLoS Pathogens, 2012. 8(10): p. e1002963.

Hajjar, A. M., et al., *Lack of in vitro* and *in vivo recognition of Francisella tularensis* subspecies *lipopolysaccharide by Toll-like receptors*. Infection and Immunity, 2006. 74(12): p. 6730-8.

Heath, D. G., et al., *Protection against experimental bubonic and pneumonic plague by a recombinant capsular F*1*-V antigen fusion protein vaccine*. Vaccine, 1998. 16(11-12): p. 1131-7.

Hirschfeld, M., et al., *Cutting edge: repurification of lipopolysaccharide eliminates signaling through both human and murine toll-like receptor* 2. Journal of Immunology, 2000. 165(2): p. 618-22.

Jones, J. W., et al., *Comprehensive structure characterization of lipid A extracted from Yersinia pestis for determination of its phosphorylation configuration*. Journal of the American Society for Mass Spectrometry, 2010. 21(5): p. 785-99.

Jones, J. W., et al., *Determination of pyrophosphorylated forms of lipid A in Gram-negative bacteria using a multivaried mass spectrometric approach*. Proceedings of the National Academy of Sciences of the United States of America, 2008. 105(35): p. 12742-7.

Jones, T., et al., *Intranasal Protollin/F*1*-V vaccine elicits respiratory and serum antibody responses and protects mice against lethal aerosolized plague infection*. Vaccine, 2006. 24(10): p. 1625-32.

Kalhorn, T. F., A. Kiavand, I. E. Cohen, A. K. Nelson, and R. K. Ernst, *A sensitive liquid chromatography/mass spectrometry-based assay for quantitation of amino-containing moieties in lipid A. Rapid Commun Mass Spectrom,* 2009. 23(3): p. 433-42.

Kanistanon, D., et al., *A Francisella mutant in lipid A carbohydrate modification elicits protective immunity*. PLoS pathogens, 2008. 4(2): p. e24.

Kawai, T. and S. Akira, *Toll-like receptors and their crosstalk with other innate receptors in infection and immunity. Immunity,* 2011. 34(5): p. 637-50.

Lai, X. H., et al., *Mutations of Francisella novicida that alter the mechanism of its phagocytosis by murine macrophages. PLoS One,* 2010. 5(7): p. e11857.

Lembo, A., et al., *Administration of a synthetic TLR*4 *agonist protects mice from pneumonic tularemia*. Journal of Immunology, 2008. 180(11): p. 7574-81.

Ma, C. S., et al., *The origins, function, and regulation of T follicular helper cells*. The Journal of Experimental Medicine, 2012. 209(7): p. 1241-53.

MacArthur, I., et al., *Role of pagL and lpxO in Bordetella bronchiseptica lipid A biosynthesis*. Journal of Bacteriology, 2011. 193(18): p. 4726-35.

Man, N., A. M. Hajjar, N. R. Shah, A. Novikov, C. S. Yam, M. Caroff, and R. C. Fernandez, *Substitution of the Bordetella pertussis lipid A phosphate groups with glucosamine is required for robust NF-kappaB activation and release of proinflammatory cytokines in cells expressing human but not murine Toll-like receptor* 4*-MD-*2*-CD*14. Infect Immun, 2010. 78(5): p. 2060-9.

Miller, S. I., R. K. Ernst, and M. W. Bader, LPS, *TLR*4 *and infectious disease diversity*. Nature Reviews Microbiology, 2005. 3(1): p. 36-46.

Meng, J., M. Gong, H. Bjorkbacka, and D. T. Golenbock, *Genome-Wide Expression Profiling and Mutagenesis Studies Reveal that Lipopolysaccharide Responsiveness Appears To Be Absolutely Dependent on TLR*4 *and MD-*2 *Expression and Is Dependent upon Intermolecular Ionic Interactions*. J Immunol, 2011. 187(7): p. 3683-93.

Parent, M. A., et al., *Cell-mediated protection against pulmonary Yersinia pestis infection*. Infection and Immunity, 2005. 73(11): p. 7304-10.

Parent, M. A., et al., *Yersinia pestis V protein epitopes recognized by CD*4 *T cells*. Infection and Immunity, 2005. 73(4): p. 2197-204.

Pasare, C. and R. Medzhitov, *Toll-like receptors: linking innate and adaptive immunity*. Adv Exp Med Biol, 2005. 560: p. 11-8.

Raetz, C. R., et al., *Lipid A modification systems in Gram-negative bacteria*. Annual Review of Biochemistry, 2007. 76: p. 295-329.

Rebeil, R., et al., *Variation in lipid A structure in the pathogenic Yersiniae*. Molecular Microbiology, 2004. 52(5): p. 1363-73.

Seregin, S. S., et al., *TRIF is a critical negative regulator of TLR agonist mediated activation of dendritic cells in vivo*. PloS One, 2011. 6(7): p. e22064.

Somerville, J. E., Jr., et al., *A novel Escherichia coli lipid A mutant that produces an antiinflammatory lipopolysaccharide*. Journal of Clinical Investigation, 1996. 97(2): p. 359-65.

Ting, Y. S., S. A. Shaffer, J. W. Jones, W. V. Ng, R. K. Ernst, and D. R. Goodlett, *Automated lipid A structure assignment from hierarchical tandem mass spectrometry data*. Journal of the American Society for Mass Spectrometry, 2011. 22(5): p. 856-66.

Yi, E. C. and M. Hackett, *Rapid isolation method for lipopolysaccharide and lipid A from gram-negative bacteria*. The Analyst, 2000. 125(4): p. 651-6.

Wang, X., et al., *Attenuated virulence of a Francisella mutant lacking the lipid A* 4'*-phosphatase*. Proc Natl Acad Sci USA, 2007. 104(10): p. 4136-41.

Wang, X., et al., *MsbA transporter-dependent lipid A* 1*-dephosphorylation on the periplasmic surface of the inner membrane: topography of Francisella novicida LpxE expressed in Escherichia coli*. Journal of Biological Chemistry, 2004. 279(47): p. 49470-8.

West, T. E., et al., *Activation of Toll-like receptors by Burkholderia pseudomallei*. BMC Immunology, 2008. 9: p. 46.

West, T. E., et al., *Inhalation of Francisella novicida Delta mglA causes replicative infection that elicits innate and adaptive responses but is not protective against invasive pneumonic tularemia*. Microbes and Infection/Institut Pasteur, 2008. 10(7): p. 773-80.

West, N. P., et al., *Non-motile mini-transposon mutants of Bordetella bronchiseptica exhibit altered abilities to invade and survive in eukaryotic cells*. Fems Microbiology Letters, 1997. 146(2): p. 263-269.

Westphal, O. and K. Juan, *Bacterial lipopoly-saccharides. Extraction with phenol-water and further applications of the procedure*. Methods in Carbohydrate Chemistry, 1965. 5(83).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A biosynthetic, immunomodulating lipid polysaccharide compound of formula (I)

(I)

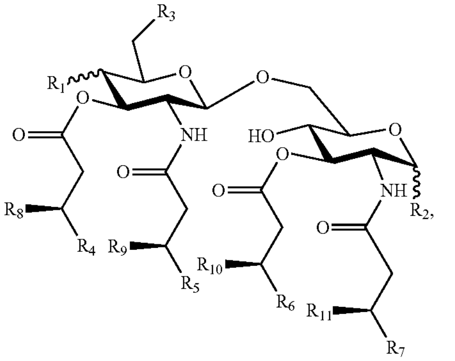

wherein $R_1$ may be H, OH, protonated phosphate, a phosphate salt, a sugar phosphonate, or a mono-, di- or poly-saccharide, $R_2$ may be H, a sugar phosphonate, or a mono-, di- or poly-saccharide, $R_3$ may be OH or a mono-, di- or poly-saccharide, $R_4$, $R_5$, $R_6$ and $R_7$ may be an alkyl or alkenyl chain from 7 to 13 carbons, and $R_8$, $R_9$, $R_{10}$ and $R_{11}$ may be H, OH, or an alkyl or alkenyl ester from 10 to 18 carbons.

2. The compound of claim 1, wherein the compound is selected from the group consisting of compounds VIII, IX, X, and XI (VIII)

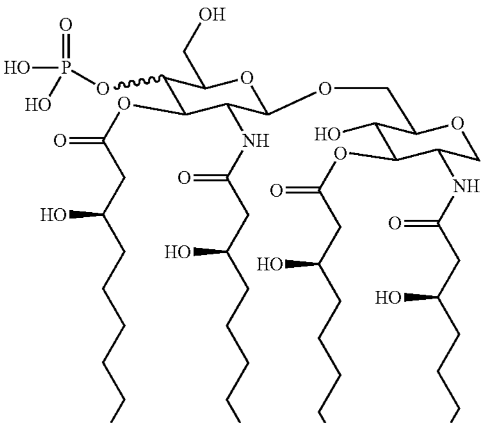

-continued

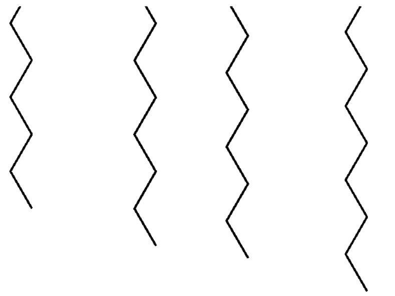

, (IX)

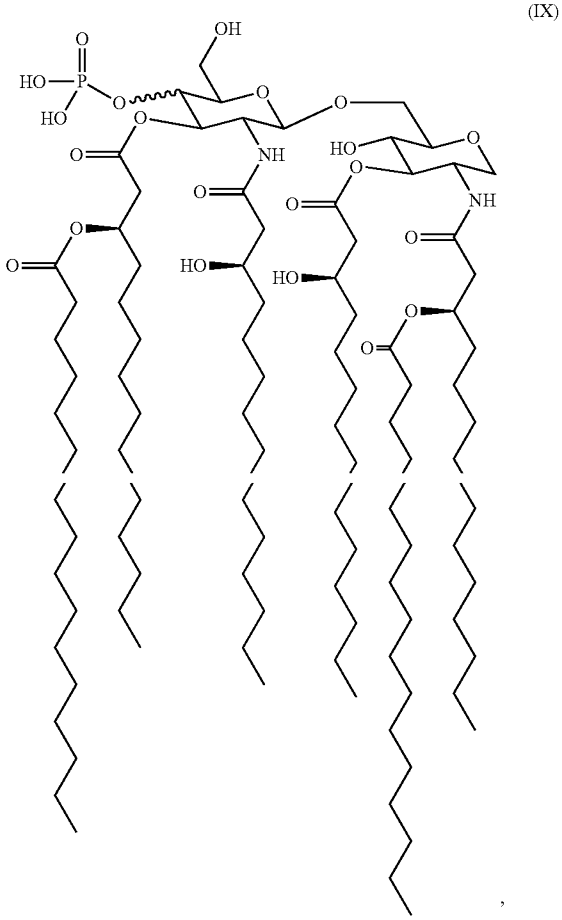

, (X)

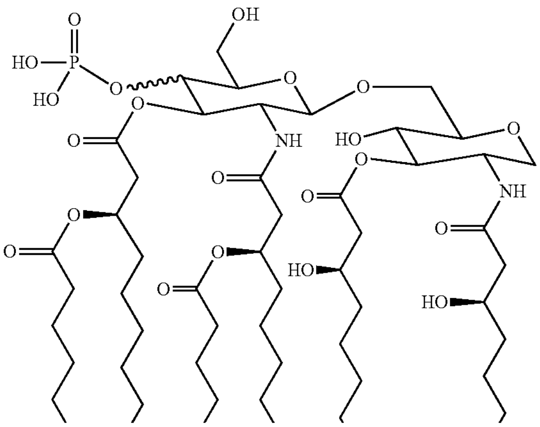

-continued
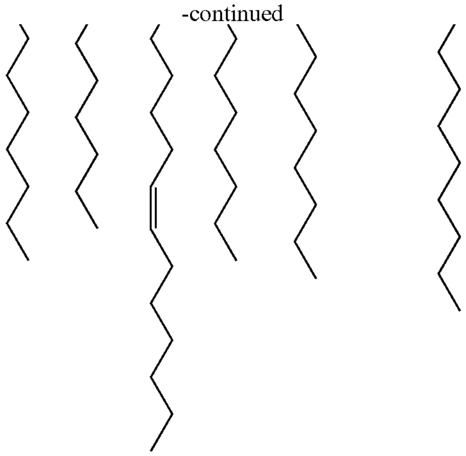
,
(XI)
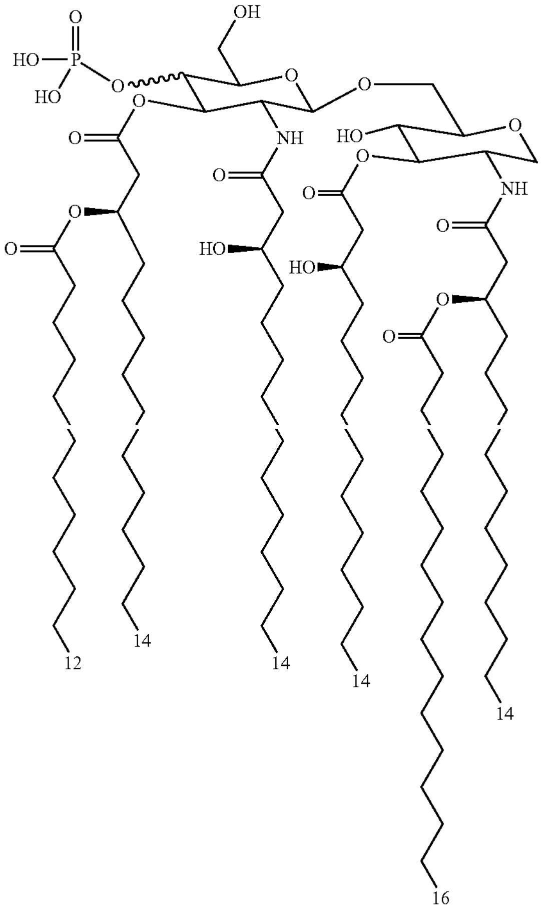
.
3. A kit, comprising one or more of the compounds of claim 1.
4. The kit of claim 3, further comprising one or both of an antigen and a pharmaceutically acceptable carrier.
5. A biosynthetic, immunomodulating lipid polysaccharide compound of the formula (XIV):
(XIV)
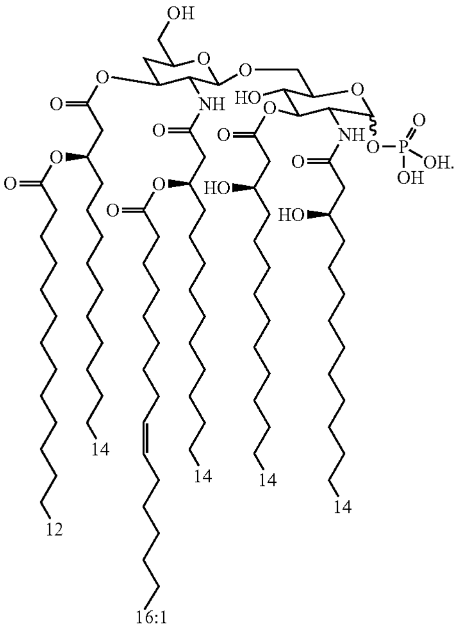
* * * * *